(12) United States Patent
Stiene et al.

(10) Patent No.: US 7,998,666 B2
(45) Date of Patent: *Aug. 16, 2011

(54) ANALYTE TEST SYSTEM FOR DETERMINING THE CONCENTRATION OF AN ANALYTE IN A PHYSIOLOGICAL OR AQUEOUS FLUID

(75) Inventors: Matthias Stiene, Gilching (DE); Ingrid Rohm, Gilching (DE)

(73) Assignee: Egomedical Technologies AG, Oberuzwil (CH)

( * ) Notice: Subject to any disclaimer, the term of this patent is extended or adjusted under 35 U.S.C. 154(b) by 380 days.

This patent is subject to a terminal disclaimer.

(21) Appl. No.: 11/659,968

(22) PCT Filed: Aug. 13, 2004

(86) PCT No.: PCT/EP2004/009113
§ 371 (c)(1),
(2), (4) Date: Jul. 24, 2007

(87) PCT Pub. No.: WO2006/015615
PCT Pub. Date: Feb. 16, 2006

(65) Prior Publication Data
US 2007/0287191 A1   Dec. 13, 2007

(51) Int. Cl.
*C12Q 1/00* (2006.01)
*G01N 15/06* (2006.01)
*G01N 25/08* (2006.01)

(52) U.S. Cl. ............. 435/4; 422/68.1; 422/73; 427/2.12; 427/209; 436/150; 600/309

(58) Field of Classification Search .................. None
See application file for complete search history.

(56) References Cited

U.S. PATENT DOCUMENTS

| 4,339,241 | A | | 7/1982 | Stöcker |
| 4,687,529 | A | * | 8/1987 | Wang ............................ 156/163 |
| 4,761,381 | A | | 8/1988 | Blat et al. |
| 4,849,340 | A | | 7/1989 | Oberhardt et al. |
| 5,144,139 | A | | 9/1992 | Hillman et al. |
| 5,628,890 | A | | 5/1997 | Carter et al. |
| 5,628,961 | A | | 5/1997 | Davis et al. |
| 5,629,209 | A | | 5/1997 | Braun et al. |

(Continued)

FOREIGN PATENT DOCUMENTS
DD            224119         6/1985
(Continued)

OTHER PUBLICATIONS

International Search Report issued on Jan. 31, 2005 in International Application No. PCT/EP2004/009113.

(Continued)

*Primary Examiner* — Krishnan S Menon
*Assistant Examiner* — Dirk Bass
(74) *Attorney, Agent, or Firm* — Fanelli Haag PLLC

(57) ABSTRACT

An analyte test element for determining the concentration of at least one analyte in a physiological sample fluid having a first and a second surface in a predetermined distance opposite from each other, said both surfaces are provided with two substantially equivalent patterns forming areas of high and low surface energy which are aligned mostly congruent, whereby the areas with high surface energy create a sample distribution system with at least two detection areas, characterized in that the detection areas of first and second surface are also provided with two corresponding patterns of working and reference electrodes of electrochemical detection means.

15 Claims, 18 Drawing Sheets

U.S. PATENT DOCUMENTS

| | | | |
|---|---|---|---|
| 5,711,861 | A | 1/1998 | Ward et al. |
| 6,165,739 | A | 12/2000 | Clatch et al. |
| 6,251,083 | B1 | 6/2001 | Yum et al. |
| 6,706,159 | B2 | 3/2004 | Moerman et al. |
| 6,922,578 | B2 * | 7/2005 | Eppstein et al. .............. 600/347 |
| 6,969,166 | B2 | 11/2005 | Clark et al. |
| 7,166,208 | B2 | 1/2007 | Zweig |
| 7,238,324 | B2 | 7/2007 | Ko et al. |
| 7,241,265 | B2 | 7/2007 | Cummings et al. |
| 7,255,780 | B2 | 8/2007 | Shenderov |
| 2002/0130042 | A1 | 9/2002 | Moerman et al. |
| 2002/0168290 | A1 * | 11/2002 | Yuzhakov et al. .............. 422/56 |
| 2003/0083385 | A1 | 5/2003 | Gerlach |
| 2003/0210287 | A1 | 11/2003 | Harding et al. |
| 2004/0007585 | A1 | 1/2004 | Griffith et al. |
| 2004/0153257 | A1 | 8/2004 | Munk |
| 2004/0241451 | A1 | 12/2004 | Clark et al. |
| 2005/0106713 | A1 * | 5/2005 | Phan et al. .................. 435/287.2 |
| 2005/0196820 | A1 | 9/2005 | Zweig |
| 2005/0203360 | A1 | 9/2005 | Brauker et al. |
| 2007/0287191 | A1 | 12/2007 | Stiene et al. |
| 2009/0221011 | A1 | 9/2009 | Stein et al. |
| 2010/0035245 | A1 | 2/2010 | Stiene et al. |
| 2010/0140116 | A1 | 6/2010 | Stiene et al. |
| 2010/0152554 | A1 | 6/2010 | Stuene et al. |

FOREIGN PATENT DOCUMENTS

| | | |
|---|---|---|
| DE | 3632379 | 3/1988 |
| DE | 19850501 | 5/2000 |
| EP | 0018435 | 11/1980 |
| EP | 0215419 | 3/1987 |
| EP | 0400460 | 12/1990 |
| EP | 0454967 | 11/1991 |
| EP | 0503914 | 9/1992 |
| EP | 0757921 | 2/1997 |
| EP | 0779226 | 6/1997 |
| EP | 0951939 | 10/1999 |
| EP | 1318397 | 6/2003 |
| EP | 1574858 | 9/2005 |
| JP | 2000-042402 | 2/2000 |
| WO | WO 89/04474 | 5/1989 |
| WO | WO 93/22453 | 11/1993 |
| WO | WO 96/39343 | 12/1996 |
| WO | WO 00/56808 | 9/2000 |
| WO | WO 01/46038 | 6/2001 |
| WO | WO 02/076878 | 10/2002 |
| WO | WO 02/085185 | 10/2002 |
| WO | WO 03/083469 | 10/2003 |
| WO | WO 2005/072216 | 8/2005 |
| WO | WO 2005/121785 | 12/2005 |
| WO | WO 2006/015615 | 2/2006 |
| WO | WO 2006/091564 | 8/2006 |

OTHER PUBLICATIONS

Koscielniak, P. "Nonlinear calibration by the standard addition method." Chemometrics and Intelligent Laboratory Systems, 47 (1999), pp. 275-287.

Bass, D., Restriction Requirement issued on Jul. 31, 2009 in U.S. Appl. No. 11/073,254, pp. 1-7.

Bass, D., Non-Final Office Action issued on Dec. 2, 2009 U.S. Appl. No. 11/073,254, pp. 1-9.

Heiss, C. et al. "Dip and Read Test Strips for the Determination of Trinitrotoluene (TNT) in Drinking Water". Analytica Chimica Acta, vol. 396(3/2), pp. 174-178 (1998).

Dosch, M. et al. "Homogeneous Immunoassay for the Detection of Trinitrotoluene (TNT) Based on the Reactivation of Apoglucose Oxidase Using a Novel Fad-Trinitrotoluene Conjugate". Fresenius Journal of Analytical Chemistry, vol. 361(2), pp. 174-178 (1998).

International Search Report and Written Opinion issued on Feb. 24, 2006 in International Application No. PCT/EP2005/009381.

European Examination Report issued on Jun. 16, 2010 in European Application No. 05 782 632.3-2404.

Haidekker, M.A. et al. "Hydrophilic Molecular Rotor Derivatives—Synthesis and Characterization" Bioorganic Chemistry, Online, vol. 4(32), pp. 274-289 (2004).

International Search Report and Written Opinion issued on Mar. 10, 2006 in International Application No. PCT/EP2008/009382.

International Search Report and Written Opinion issued on Apr. 2, 2008 in International Application No. PCT/EP2007/011026.

International Search Report and Written Opinion issued on Apr. 4, 2008 in International Application No. PCT/EP2008/000679.

English translation of Abstract of DD 224119.

Heiss, C., et al., Analytica Chimica Acta, vol. 396(2/3), pp. 309-316, 1999.

Bass, D., Notice of Allowance dated Aug. 27, 2010 issued in U.S. Appl. No. 11/073,254.

* cited by examiner

| | A | B | C | n |
|---|---|---|---|---|
| I | | | 1st Order (linear) | 3 |
| II | | | 2nd Order (quadratic) | 4 |
| III | | | 3rd Order (cubic) | 5 |
| IV | | | 4th Order | 6 | n: minimum number of measurements required for calibration model in column C

Fig. 6

ANALYTE TEST SYSTEM FOR DETERMINING THE CONCENTRATION OF AN ANALYTE IN A PHYSIOLOGICAL OR AQUEOUS FLUID

The present application is a U.S. National Phase Application under 35 U.S.C. §371 of International Application PCT/EP2004/009113, which was filed Aug. 13, 2004, which is hereby incorporated by reference in its entirety.

FIELD OF THE INVENTION

This invention relates to the field of quantitative analysis of an analyte, e. g. glucose, in a physiological fluid, e. g. blood. More particularly, this invention provides an analyte test system and test method for the quantitative determination of analytes in a physiological or aqueous fluid and a method of preparation.

BACKGROUND OF THE INVENTION

The determination of analyte concentrations in physiological samples plays a prominent role in diagnosis and therapy of a variety of diseases. Analytes of interest include among others glucose, cholesterol, free fatty acids, triglycerides, proteins, ketones, phenylalanine, enzymes, antibodies, or peptides in blood, plasma, urine or saliva.

Measuring the glucose concentration in samples of whole blood is a particularly common task. Since Diabetes causes dangerous physiological complications leading to the loss of vision, kidney failure and other serious medical consequences. Only a stringent therapy and disease management minimises the risk of these consequences with adjustments on exercise, diet, and medication. Some patients have to test their blood glucose concentration frequently with three or more measurements a day. These patients as well as clinicians and hospitals require an accurate, reliable, and ideally inexpensive method to adjust their treatment regimes to avoid the long-term complications of diabetes mellitus.

The increased awareness about diabetes, the acceptance of self-monitoring and self-treatment have been dependent upon the availability of suitable devices and let to the development of a multitude of devices and methods for personal use and point of care testing as well. Available are pregnancy, ovulations, blood coagulation, ketone and cholesterol tests, as example for a non-exhaustive selection, but most prominent in the area of self-monitoring is still the detection of glucose in capillary blood.

Typically, a physiological sample fluid, e. g. capillary blood, is applied to a test strip to evaluate the concentration of an analyte. The test strips are usually used in conjunction with a measuring device which measures light reflectance and/or transmittance, if the strip is designed for photometric detection, or some electrical properties, such as electrical current, if the strip is designed for detection of an electro-active compound.

Over the last couple of years electrochemical biosensors became more and more prominent on the diagnostic market and provide the patient with several advantages over the reflectance photometry systems. Main differences are the capillary fill features of the test strips allowing an easier sample application in comparison of the top fill membrane based reflectance photometry systems. Additionally, the measurement cell can be located at the tip of the strip thus the blood sample will not be in direct contact with the measurement device (meter) during the test procedure, which keeps the device clean and hygienic avoiding blood contamination of the meter.

Until today a wide variety of electrochemical biosensor strips has evolved. An exemplary electrochemical biosensor as disclosed in U.S. Pat. No. 5,288,636, includes a working and a counter/reference electrode. A reagent, which includes an enzyme capable of catalyzing a reaction involving a substrate for the enzyme, a redox mediator capable of transferring electrons transferred between the enzyme and the working electrode, and a buffer, is located at the working electrode surface. When a sample fluid containing the analyte to be measured is added to the reagent, a reaction occurs that oxidizes the analyte and reduces the redox mediator. After or during this reaction, an electric potential difference is applied between the electrodes. The current produced by the electrooxidation of the reduced form of the mediator is measured and correlated to the amount of the analyte in the sample.

In a typical embodiment, the electrochemical system consists of two electrodes on a support member enclosed by supporting walls to form a cavity which is either small enough to be filled by capillary action (U.S. Pat. No. 4,900,424; Birth et al., 1987), or with help of a spreading or mesh layers (U.S. Pat. No. 5,628,890; Carter et al., 1997).

Due to the raw material and process variations in large-scale manufacture of the analyte strips an adequate strip-to-strip reproducibility from one batch to the next is not guaranteed. Therefore, all known systems require test strips, which have to be calibrated during the production process. This calibration information is provided by the time of use to the meter by manual or automatic means. In the first case the user has to enter the calibration information in form of a number with comes with each lot of test strips, in the second case the information is encoded in the strip either by bar, colour, or a digital coding feature. Therefore this type of calibration information represents the functional characteristic of the test strip by the time of production, which may or may not be different for the test strip characteristics by the time of use that could be up to two years later.

Furthermore, the measuring procedure may be impaired by other variable factors in the physiological sample fluid. A typical complication in whole blood analysis is the variability of erythrocyte levels, leading to results which may not reflect the real analyte concentration of the sample.

PCT/EP 2004002284 discloses a dry reagent test strip for the photometric detection and quantitative determination of an analyte in a physiological fluid which is provided with an integrated calibration system using the standard addition method.

However, up to now no analyte test system exists, which is suitable for electrochemical detection and quantitative determination of an analyte in a physiological fluid and which is provided with integrated calibration and quality control means.

Therefore, it is the object of the present invention, to provide an analyte test system with an integrated calibration means, which accounts for and compensates any variability may it be generated by fluctuations in the production process or by the variability of the analysed sample itself, which has electrochemical detection means for measuring the concentration of an analyte in a physiological fluid sample.

It is a further object of the present invention, to provide a production process for the electrochemical analyte test element which does not involve many and complicated production steps and therefore is inexpensive and usable for products assisting patients in self-monitoring blood glucose or other important physiological parameters.

SUMMARY OF THE INVENTION

This invention provides an element for determining the concentration of an analyte like glucose, cholesterol, free fatty acids, triglycerides, proteins, ketones, phenylalanine or enzymes, in a physiological fluid like blood, serum, plasma, saliva, urine, interstitial and/or intracellular fluid, the device incorporating calibration and quality control means with electrochemical detection means in a dry reagent test strip. The production of the inventive analyte test element involves only a small number of uncomplicated production steps enabling an inexpensive production of the strips.

Due to the integrated calibration procedure the analyte test system of the present invention provides reliable results regardless of the blood type, haematocrit level, temperature etc. In addition, production variations are compensated by the integrated calibration procedure as well. Moreover, active component aging is detectable and can be compensated and/or reported which will lead to a prolonged shelf live of the product under suitable storage conditions.

The present invention provides an analyte test element for determining the concentration of at least one analyte in a physiological sample fluid having a first and a second surface in a predetermined distance opposite from each other, said both surfaces are provided with two substantially equivalent patterns forming areas of high and low surface energy which are aligned mostly congruent, whereby the areas with high surface energy create a sample distribution system with at least two detection areas, characterized in that the detection areas of first and second surface are also provided with two corresponding patterns of working and reference electrodes of electrochemical detection means.

The sample distribution system contained in the inner part of the analyte test element has no mechanical and/or structural features resembling walls, groves, or channels to guide the physiological fluid to the detection areas which leads to an easy, cost efficient and reliable production process.

In another aspect, the invention provides a method for preparing the analyte test element of the present invention with the steps:

applying a pattern of working electrodes on a first layer having a first surface, applying a corresponding pattern of reference electrodes on a second layer having a second surface, generating areas of high and low surface energy on the first layer having the first surface, generating a corresponding pattern of areas of high and low surface energy on the second layer having the second surface, the areas of high surface energy forming a hydrophilic sample distribution system with n predetermined detection areas, whereby n is an integer number larger than 2, whereby the working and reference electrodes are located underneath the n predetermined detection areas of the hydrophilic sample distribution system, coating a catalytic formulation on the n detection areas of the first surface, said catalytic formulation promoting the detection of an analyte concentration contained in a physiological fluid sample using electrochemical detection means, coating n calibration formulations on n detection areas of the second surface, said n calibration formulations made up of m blank formulations and n−m formulations with different levels of calibration compound, whereby m is an integer number of at least 1, and n>m, which is identical or substantially equivalent to the analyte and able to induce the same chemical reaction in the catalytic formulation as the analyte in the physiological fluid sample, applying the layers of first and second surfaces to the opposite sites of a centre layer having a discontinuity which provides a cavity for the sample distribution system formed by the areas of high surface energy on the first and second surfaces of the base and cover layer.

The analyte test element is described in several embodiments suitable for a variety of calibration procedures and adaptable to different analytes and electrochemical determination methods; it is easily integrated in test strips used for a single measurement or in more complex arrangements such as analyte test disks or bandoliers to provide base units for several measurements.

Other features and advantages of the present invention and the preferred embodiment thereof will become apparent from the following description in conjunction with the attached drawings.

BRIEF DESCRIPTION OF THE DRAWINGS

FIG. 6 shows different embodiments of the sample distribution system with different patterns of pathways and detection areas suitable for different calibration methods.

Figure 4:
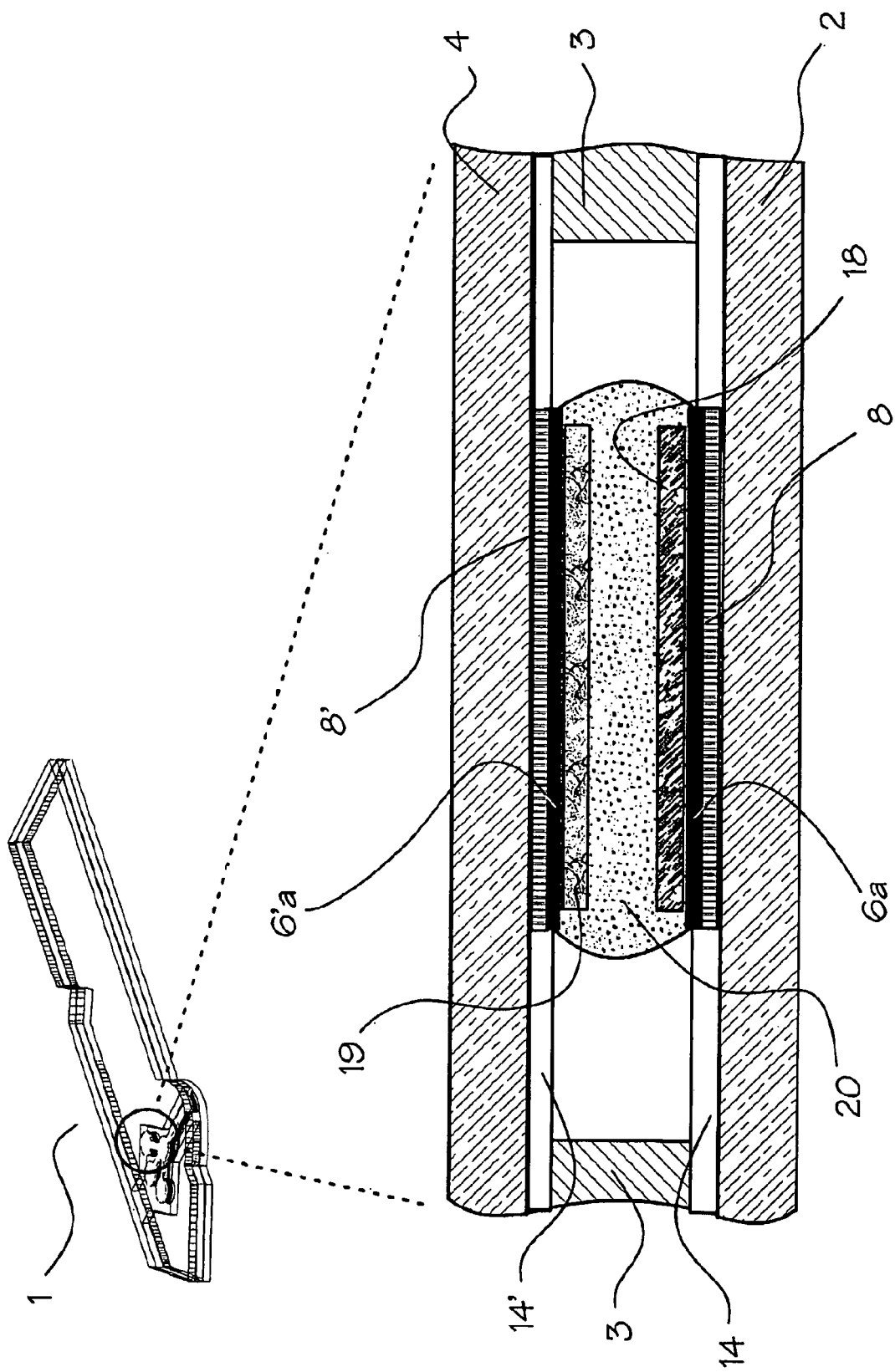
FIG. 4 is a sectional view of a detection area of the sample distribution system of the analyte test element.

The layers shown in FIG. 4 are not to scale, in particular the thickness of the layers 6, 14, 18 and 19 are largely exaggerated.

DETAILED DESCRIPTION OF THE INVENTION

Figure 1:
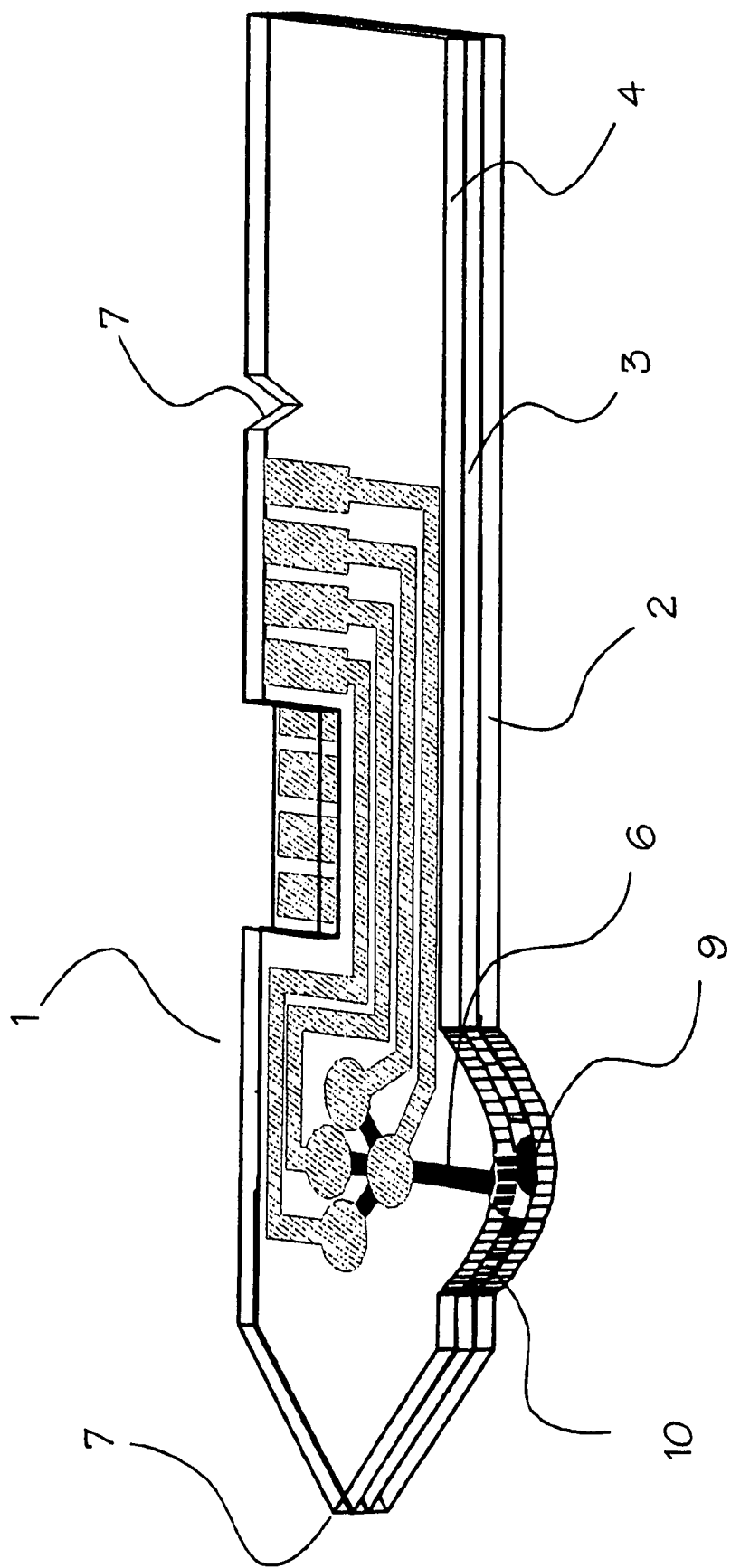
FIG. 1 is a perspective view of one embodiment of the analyte test element of the present invention provided in shape of a test strip.

FIG. 1 shows the analyte test element of the present invention in shape of a test strip 1 comprising a base layer 2, a centre layer 3 overlaying the base layer 2, and a cover layer 4 overlaying the centre layer 3. The centre layer 3 presents a discontinuity 5 (see FIG. 2), which creates a hollow cavity in conjunction with the base layer 2 and the cover layer 4. Within said cavity there is located a sample distribution system 6 which is connected to a sample application area 9 located on one side of the analyte test strip. The sample application area 9 as interface to the user is preferably formed by a convex extrusion 10 extending from one major side of the analyte test strip to allow easy application of the sample. Opposite to the sample application area 9 on the second major side of the analyte test strip is the location of an air vent (not shown) allowing the displacement of air while the physiological fluid is distributed to the sample distribution system.

Figure 2:
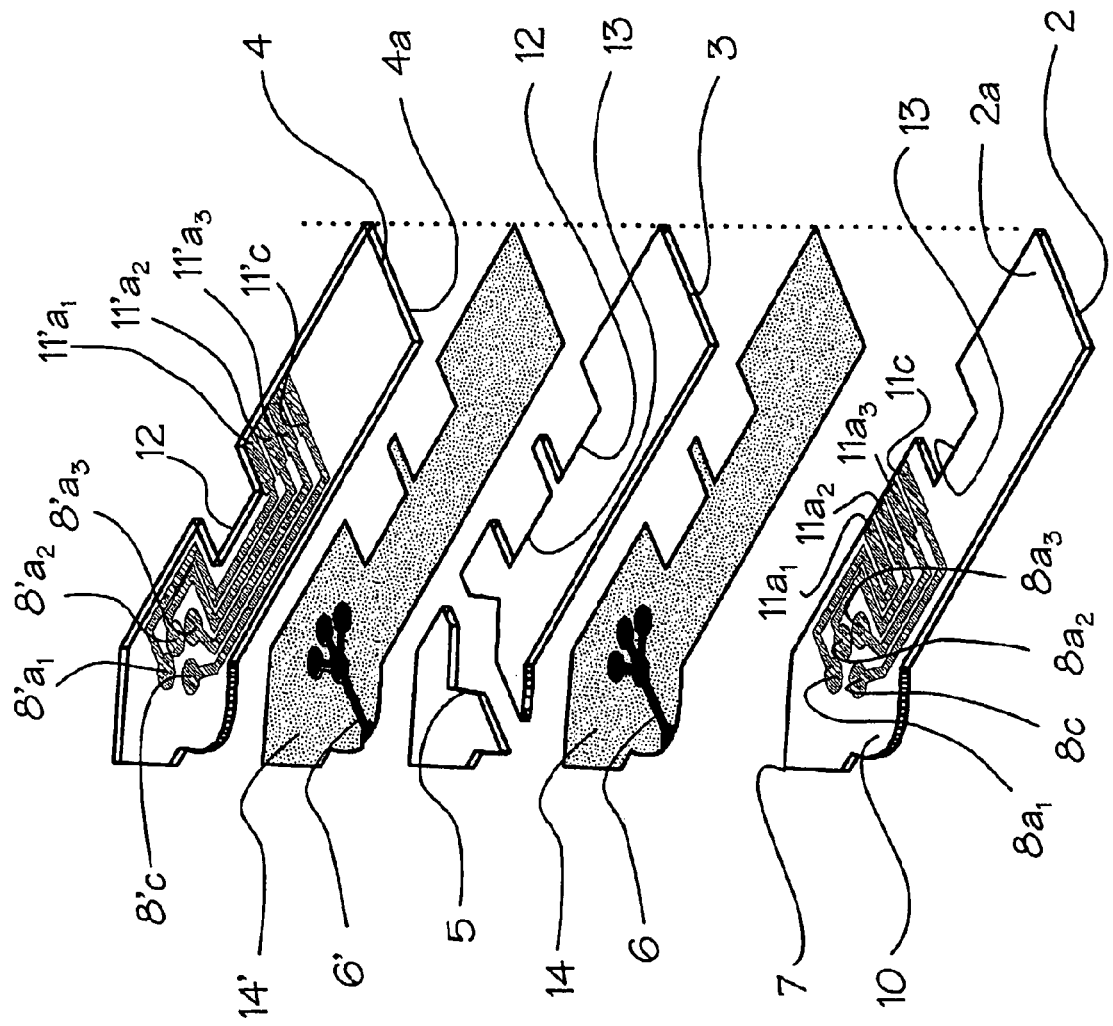
FIG. 2 is an exploded perspective view of the element according to FIG. 1 showing the different layers separately.

In addition, the analyte test strip 1 possesses registration features 7 useful to differentiate between several kinds of analyte test strips e. g. for the determination of different analytes. By this means, a multi-analyte meter could be instructed to run a special program or procedures with selectable parameters upon strip insertion required for the determination of a particular analyte. As illustrated in FIG. 2, which represents the multi-layer arrangement of FIG. 1 in an exploded view, the base layer 2 provides a first surface 2a providing the substrate for the working electrodes 8, conductive tracks and contacts 11 of a electrochemical detection means, and the cover layer 4 provides a second surface 4a providing the substrate for corresponding reference electrodes 8', conductive tracks and contacts 11' of a electrochemical detection means.

Additionally, the first surface 2a of the base layer 2 is provided with a first hydrophilic pattern 6 forming a first part of a sample distribution system. The hydrophilic pattern 6 is surrounded by a hydrophobic insulating layer 14 which serves as hydrophobic "guiding element" for the sample fluid in the sample distribution system and as electrical insulation for the leads, which connect the working electrodes 8 to the electrochemical detection means. Also, the second surface 4a of the cover layer 4 is provided with a corresponding hydrophilic pattern 6' forming the second part of a sample distribution system. The hydrophilic pattern 6' is also surrounded by a hydrophobic layer 14', which serves as hydrophobic guiding element for the sample fluid and as electrical insulation for the leads connecting the reference electrodes 8'.

The hydrophilic patterns 6, 6' forming areas with high surface energy of the sample distribution system comprise a predetermined number of analyte detection areas 6a, 6'a and sample pathways 6b, 6'b (see FIG. 3), which are aligned and registered mostly congruent upon assembly of the multi-layer arrangement. Moreover, the working and reference electrodes 8, 8' match with the detection areas 6a, 6'a of the sample distribution system created by the hydrophilic patterns 6, 6' formed on the base and cover layers.

Base and cover layer are separated by the centre layer 3, which defines the distance between the first surface 2a of the base layer 2 and the second surface 4a of the cover layer 4 and the electrode systems 8 and 8'. The centre layer 3 might be constructed from a thin polymer film coated with an adhesive layer on either side but might be realised by a printed layer or other layers respectively spacers, which provide the desired room between the first surface 2a of the base layer 2 and the second surface 4a of the cover layer 4. For the functionality of the analyte test element it is only important that the centre layer provides a precise and exact definition of the distance between base and cover layer.

The centre layer 3 has a discontinuity 5 to form a hollow cavity together with the first surface 2a of the base layer 2 and the second surface 4a of the cover layer 4. The sample distribution system which will be formed by the hydrophilic patterns 6, 6' and the surrounding patterns of the hydrophobic insulation layers 14, 14' on the first surface 2a respectively the second surface 4a is located within the cavity created by the discontinuity 5 of the centre layer 3 and the first surface 2a of the base layer 2 and the second surface 4a of the cover layer 4. Preferably, the hollow cavity is substantially larger by design than the sample distribution system. Within a functional analyte test element the applied sample fluid enters the measurement chamber on the hydrophilic pathway (area with high surface energy) of the sample distribution system formed by the hydrophilic patterns 6 and 6' and is constrained by the hydrophobic insulation layers 14 and 14' (areas with low surface energy) within the predetermined flow paths 6b, 6'b and detection areas 6a, 6'a (see FIG. 3) of the sample distribution system between the first surface 2a of the base layer 2 and the second surface 4a of the cover layer 4. Accordingly, the sample will not fill the entire cavity of the analyte test element and allows therefore very small sample volumes of less than 0.5 µL even with multiple working electrodes.

Since the purpose of the discontinuity 5 of the centre layer is only to create a cavity for the sample distribution system formed by the hydrophilic patterns 6, 6', the discontinuity 5 of the centre layer 3 can have different forms, such as umbrella shape, rectangular shape or circular shape. The discontinuity 5 of the centre layer 3 does not influence the size of the sample distribution system formed on the hydrophilic patterns 6, 6' and therefore does not influence or change the required sample volume. Compared to the sample distribution system patterns 6, 6', the cavity shapes are rather simple, thus allowing the application of simple punch tools and fast processing with less demand on the registration accuracy.

Additionally, the centre layer 3 is provided with a first recess 12 to expose the contacts 11 of the working electrodes 8a of the base layer, and a second recess 13 to expose the contacts 11' of the reference electrodes 8'a of the cover layer.

Figure 3:
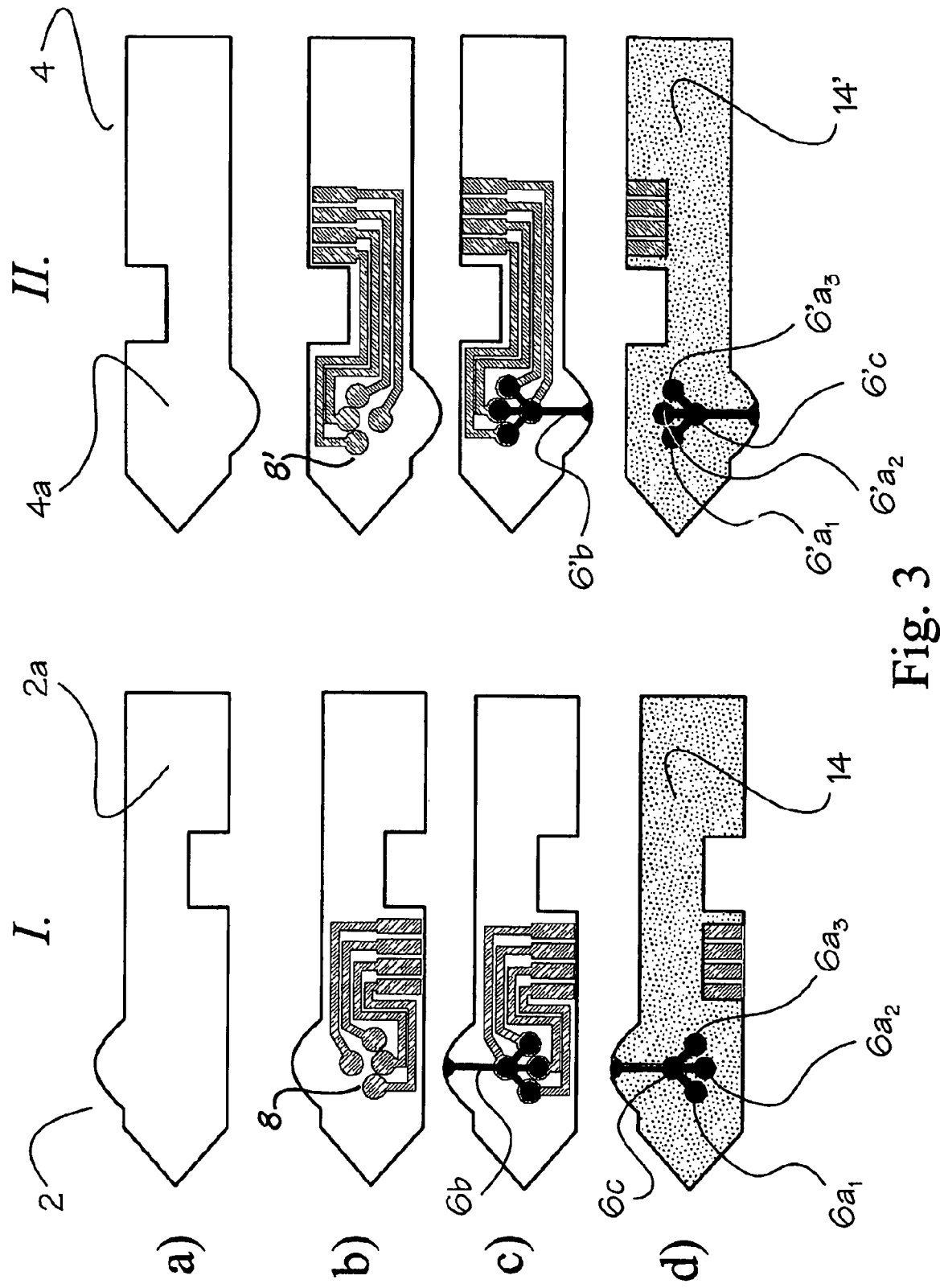
FIG. 3 shows the sequential coating of the different layers onto the base and cover layers.

FIG. 3 shows the construction steps of a preferred embodiment of the analyte test element of the present invention. The primary step as shown in row a) is the preparation of the base layer 2 providing a first surface 2a and the cover layer 4 providing a second surface 4a. The base layer and cover layer are typically formed from a solid polymer film. Within certain embodiments it is advantageous to select transparent polymer films as substrate to allow the patient to monitor the filling of the analyte test element of the analyte test strip, however it is not required for the proper function of the analyte test system.

This process step is followed by the application of the electrodes and the conductive tracks (row b). In the embodiment of the present invention according to FIG. 3, the working electrodes 8 of the electrochemical detection means are applied onto the first surface 2a of the base layer 2 and the corresponding reference electrodes 8' of the electrochemical detection means are applied onto the second surface 4a of the cover layer, but as a matter of course, the working electrodes 8 of the electrochemical detection means can be applied onto the second surface 4a of the cover layer 4 and the corresponding reference electrodes 8' of the electrochemical detection means can be applied onto the first surface 2a of the base layer. Moreover, it is possible to electrically connect all or some of reference electrodes to each other.

Several technologies are known in the art and used in the industry to produce conductive patterns of tracks and electrodes, which can be adopted for this step. Suitable are screen printing of carbon or noble metal inks, physical or chemical vapour deposition of noble metals or carbon with subsequent laser or photolithographic patterning of the required circuit structure, or chemical deposition of noble metals on compatible surfaces. Clean noble metal structures such as gold, palladium, and platinum produced in a vapour deposition process are most suitable for a reliable and reproducible electrochemical measurement. In a preferred embodiment, the element is formed from a polyester substrate such as MYLAR® or MELINEX®' coated with gold or most preferably with palladium. The required circuit structure is preferably produced by ablation of the metal layer with a YAG laser.

The long wavelength of the laser (1064 nm) primarily evaporates the metal and leaves the polymer film intact, thus the structuring process is very efficient and avoids contamination of the metal layer with burned plastic particles.

After completion of the circuit structure the first surface $2a$ of the base layer 2 and the second surface $4a$ of the cover layer 4 are supplied with equivalent hydrophilic patterns 6, 6' representing the areas of high surface energy, which are wettable by the sample fluid (see row c). The hydrophilic patterns 6, 6' are applied in such a manner, that the electrodes 8, 8' match with the detection areas $6a$, $6'a$ of the sample distribution system. The preparation of the base and cover layer is concluded by printing a hydrophobic insulation layer 14, 14' (row d), which serves the double purpose of insulating the parts of the conductive circuit, exposing only the electrodes and the contact pads, and restricting the sample fluid to the hydrophilic part of the sample distribution system. Additionally, the hydrophobic inks could be used to decorate the analyte test system with a desired colour, informational text or a product logo. Most preferably, these printing steps are accomplished by flexography. However, other printing or coating processes such as gravure, lithography, offset, inkjet or solid ink printing technology are suitable for the application of the hydrophilic and hydrophobic layers as well. Whereas, the solid ink printing technology is ideally suited for the application of the hydrophobic patterns due to the waxy character of the solid inks itself.

The flexography allows high-resolution printing on a rotary press and supports high-speed production. It is an established technology for printing on polymer film substrates and widely used in the packaging industry. Low viscous inks are preferred to achieve a thin and even coating of about 2-4 microns. The operation of a four-colour flexography-printing machine is established practice and provides no operational problems. Even though solvent based or UV curing inks are applicable to manufacture analyte test strips, electron beam (EB) curing inks are much preferred. These inks provide highest resistance to mechanical and chemical factors, and contain 100% polymers optionally with pigments but no volatile organic solvents and photo initiators, which have proven to affect the stability of sensor chemistry. These positive gains in performance characteristics are derived from the ability of electrons to form crosslinked polymeric films and to penetrate the surface.

Inks used in EB curing make use of the polymerizing capability of acrylic monomers and oligomers. Acrylic chemistry has a special significance in modern day inks. (6 J. T. Kunjappu. "The Emergence of Polyacrylates in Ink Chemistry," Ink World, February, 1999, p. 40.) The structure of the simplest acrylic compound, acrylic acid, is shown in the equation below.

$$CH_2=CH-COOH$$

The double bond in the acrylic moiety opens up during interaction with electrons (initiation) and forms a free radical that acts on other monomers forming a chain (propagation) leading to high-molecular-weight polymers. As mentioned above, radiation induced polymerisation requires no external initiator since radiation itself generates free radicals with the result that no initiating species will be left in the coating.

A variety of acrylic monomers are available for EB curing that range from simple acrylates such as 2-phenoxyethyl acrylate and isooctyl acrylate to prepolymers like bisphenol A epoxy acrylate and polyester/polyether acrylates (R. Golden. J. Coatings Technol., 69 (1997), p. 83). This curing technology allows the design of "functional inks" with the focus on the desired chemical and physical properties without the necessary of solvent and curing systems required by other inks, which may complicate the design process.

Inks with hydrophilic functions can be realised from a wide selection of cross-linkable water-soluble polymers, e. g. polyalcohols, glycols, polyethylene oxides acrylate derivates, vinylpyrolidone and others. Particular interesting are organo-modified silicone acrylates, which are a cross-linkable species of organo-modified polysiloxanes. A typical hydrophobic ink will contain monomers, oligomers, and prepolymers with hydrophobic functions like isooctyl acrylates, dodecyl acrylates, styrene derivates or systems with partly fluorinated carbon chains.

After completion of the base and cover layer with all the required conductive, hydrophilic and hydrophobic coatings, the catalytic formulations and the calibration formulations of the analyte test element are dosed on the predetermined detection areas ($6a$ and $6'a$). In the embodiment of the test element according to FIG. 3, the detection areas $6a_1$, $6a_2$ and $6a_3$ of first surface are coated with the catalytic formulations containing an enzyme and a mediator, whereas one detection area ($6c$) remains uncoated. The corresponding detection areas $6'a_1$, $6'a_2$ and $6'a_3$ are coated with the calibration formulations. Two of the detection areas (e. g. $6'a_2$ and $6'a_3$) are coated with calibration formulations containing different concentrations of the calibration compound, whereas the formulation coated on the third detection area (e. g. $6'a_1$) contains no calibration compound. Again, detection area ($6c$) remains uncoated for the background evaluation.

FIG. 4 is a sectional view of a detection area of the sample distribution system showing a working electrode 8 and a hydrophilic layer $6a$ of the first part of the sample distribution system applied on the base layer 2 and coated with the enzyme-mediator-layer 18, and a corresponding reference electrode 8' and a hydrophilic layer $6'a$ forming the second part of the sample distribution system applied on the cover layer 4 and coated with a calibration formulation 19. The sample fluid 20 is wetting the areas with high surface energy formed by the hydrophilic layers $6a$ and $6'a$ and is constrained in the sample distribution system by the hydrophobic insulating layers 14 and 14'.

The accuracy of the deposition of the catalytic and calibration formulations is very critical and defines the performance of the analyte test system. Preferably, both formulations are applied with aid of high precision ink-jet systems or piezoelectric print heads. The ink is mostly composed from water and the catalytic or calibration compound and will be dried at slightly elevated temperatures. Main aspect of these ink formulations is the fast reconstitution of chemical components after sample application without compromising the hydrophobic areas of the analyte test system.

Suitable catalytic formulations for the present invention are based on a non-reactive base, electron transfer components (mediators), and an enzyme or enzyme combinations as promoter. The non-reactive base provides a carrier, which needs to be suitable for ink jet printing, enzyme stabilisation and fixation to the surface of the detection areas. An exemplary composition for 100 mL formulation is given below

| Non-reactive base: | | |
|---|---|---|
| Distilled water | 65 ml | Solvent |
| Citric acid | 2.4 g | Buffer system |
| Sodium citrate 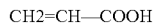 2H$_2$O | 3.2 g | Buffer system |
| Polyethylene glycole | 1.0 g | Crust inhibitor |
| BSA | 3.0 g | Enzyme stabilization |

-continued

Non-reactive base:

| Gafquat 440 (ISP) | 1.0 mL | Film forming agent |
| Advantage S (ISP) | 1.0 g | Film forming agent |
| PVA (low mol. weight) | 1.5 g | Enzyme stabilization |

Adjust pH to 6.5 and fill up to 100 mL

Catalytic formulation:
(all components are added to 100 mL non-reactive base)

| GOD (*Aspergillus niger*) | 2.0 g (250 U/mL) |
| Potassium hexacyanoferrate (III) | 2.2 g |

The catalytic formulation depends on the analyte to be detected. In case of glucose determination, the formulation can be composed with glucose oxidase (GOD) and potassium hexacyanoferrate (III) as exemplary mediator. The selected mediator might be changed for other applications or if the assay is adapted to different enzymes and analytes. Examples for frequently employed mediator systems are: potassium hexacyanoferrate (III), tetracyano-p-quinone-di-methane (TCNQ), methylviologen ($MV2^+$), tetrathiafulavlene (TTF), N-methylphenzinium ($NMP^+$), 1,1'-dimethylferrocen, ruthenium (III) hexamine, osmium bipyridine, ferrocene and their derivates.

Different enzymes and mediators might require the adjustment of the pH of the non-reactive base as well. Alternatively, potassium hexacyanoferrate (III) could be used with glucose dehydrogenase pyrrole-quinoline-quinone (GDH-PQQ) instead of GOD. Sensors with GDH (glucose dehydrogenase) enzyme show similar performance as sensors with GOD enzyme with reduced oxygen sensitivity but with a higher cross-reactivity to galactose and maltose.

Suitable inks for the calibration formulation can be composed of the non-reactive base with the required concentration of calibration compound. Preferably, the calibration compound contained in the calibration formulation 19 coated on the predetermined detection areas 6a of second surface 4a is identical or substantially equivalent to the analyte and able to induce the same chemical reaction in the catalytic formulation as the analyte in the physiological fluid sample. In case the analyte of interest in the physiological sample is glucose then the calibration compound is preferably glucose as well.

After completion of all printing and coating steps the article can be assembled in two ways. The first one aligns three separate layers: the centre layer goes on the base layer and the application of the cover layer finishes the lamination process. Tight xy registration of base and cover layers becomes a critical task for the function of the analyte test element, if this registration is not achieved, the sample distribution system will not function properly. Registration tolerances should be within +/−5% of the width of the hydrophilic pathways to achieve good performance. The application of the centre layer, a double-sided adhesive tape with a preferred thickness of 50 to 80 microns, is less demanding because of the relatively large discontinuity in the material compared to the size of the hydrophilic pathways.

Alternatively, a special printing process could be used to apply 50 to 80 microns of ink paste to realize the centre layer. Electron beam cured inks are most preferred for this alternative centre layer construction due to the minimal shrinkage of the inks during the curing process. Compared to the thickness variation of high quality adhesive tape this alternative printing process might result in a higher variability of the centre layer thickness.

Registration is especially demanding in continuous production lines where the substrate progresses with several meters up to tens of meters per minute. Substrate expansion and web tension make the registration in x-direction (the direction of the web) more difficult than the y-direction perpendicular to the web movement. FIG. 5 illustrates a solution for this problem; here cover and base layer are printed on one substrate. Thus the position of the predetermined detection areas and flow paths of the sample distribution system are fixed relative to each other and remains unaffected by the material expansion and web tension.

Figure 5A:
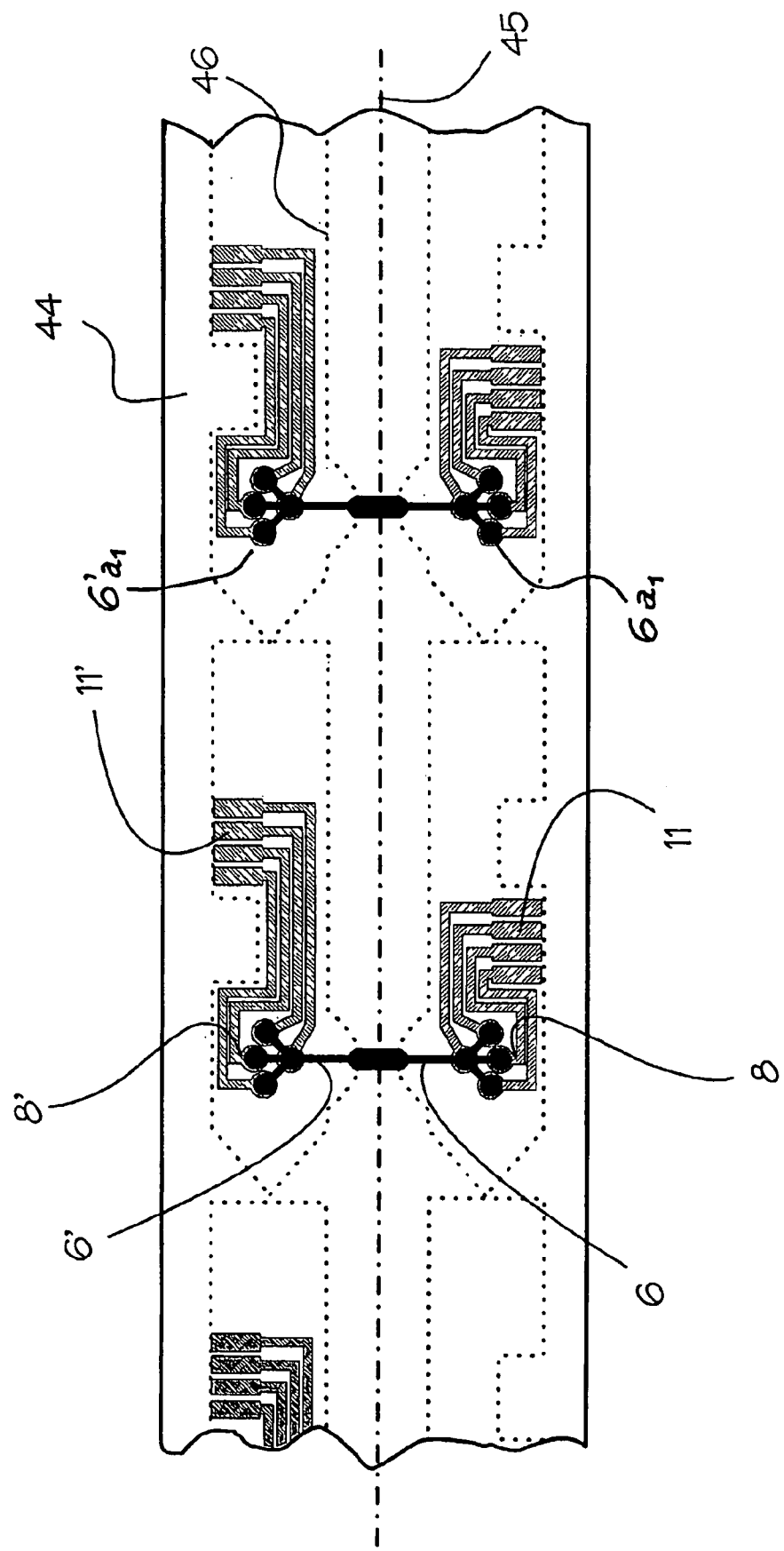
FIG. 5a to 5d show the steps of a continuous web production process of analyte test elements with strip shape.

In a first production step of the continuous web production process according to FIG. 5*a*, patterns of the working and reference electrodes 8, 8' of the electrochemical detection means and hydrophilic patterns 6, 6' of the sample distribution system are printed on one web substrate 44 forming the base and cover layer. As illustrated in FIG. 5*a*, the printed patterns of the sample distribution systems 6, 6' are arranged on the web substrates 44 opposite to each other and linked in the areas which form later the sample application areas. Thus, the positions of the working and reference electrodes 8, 8' and the predetermined detection areas 6*a*, 6'*a* are fixed relative to each other and remain unaffected by the material expansion and web tension.

In an alternative embodiment only one of the first and second surface is provided with the hydrophilic/hydrophobic (6, 14) pattern to create the sample distribution system. In a preferred embodiment, either the first or second surface is provided with the hydrophilic/hydrophobic pattern (6, 14) whereas the corresponding surface provides a homogeneous pattern of hydrophilic pixels surrounded by a hydrophobic area thereby creating a surface with semi hydrophilic and semi hydrophobic character (amphiphilic character), and eliminating the necessity to align the hydrophilic and hydrophobic pattern (6, 14) of the first surface with an equivalent hydrophilic and hydrophobic pattern (6', 14') of the second surface. The properties of such an amphiphilic surface can be easily designed by the geometric pattern of the hydrophilic pixels and the overall ratio between the hydrophilic and the hydrophobic area. In the disclosed invention the amphiphilic character, respectively the ratio between hydrophilic pixels and hydrophobic areas, is designed that the sample fluid progresses from hydrophilic pixel to hydrophilic pixel only if the opposite surface provides hydrophilic character. If the opposite surface provides hydrophobic character the movement of the fluid within the capillary gap of the analyte test element will stop. This mechanism allows the above-described method to form a functional analyte test element without the stringent requirement of precise registration of the corresponding pattern of the sample distribution system provided on the first and second surface. However, most preferably both the first and the second surface are provided with equivalent patterns of high and low surface energy to ensure swift and precise distribution of the sample fluid within the hydrophilic pathways of the sample distribution system.

The dotted lines 46 indicate the future cutting lines to segregate the analyte test strips, while the dotted lines 45 indicate the future fold line of the web substrate.

After printing the patterns of working and reference electrodes, the hydrophilic patterns of the sample distribution system and the hydrophobic insulating layer, the detection areas 6*a*, 6'*a* of the sample distribution system are coated with the catalytic and calibration formulations. For example, the detection areas 6*a* of the lower row of the web substrate 44, which will represent the first surface of the analyte test element, are coated with the catalytic formulation containing the enzyme and a mediator, whereas the detection areas 6'*a* of the upper row of the web substrate 44, which will represent the second surface of the analyte test element, are coated with calibration formulations containing different levels of the calibration compound. One of the calibration formulation (e. g. positioned in 6'*a*$_1$) does not contain calibration compound and delivers the reading of the physiological fluid in the detection step.

Figure 5B:
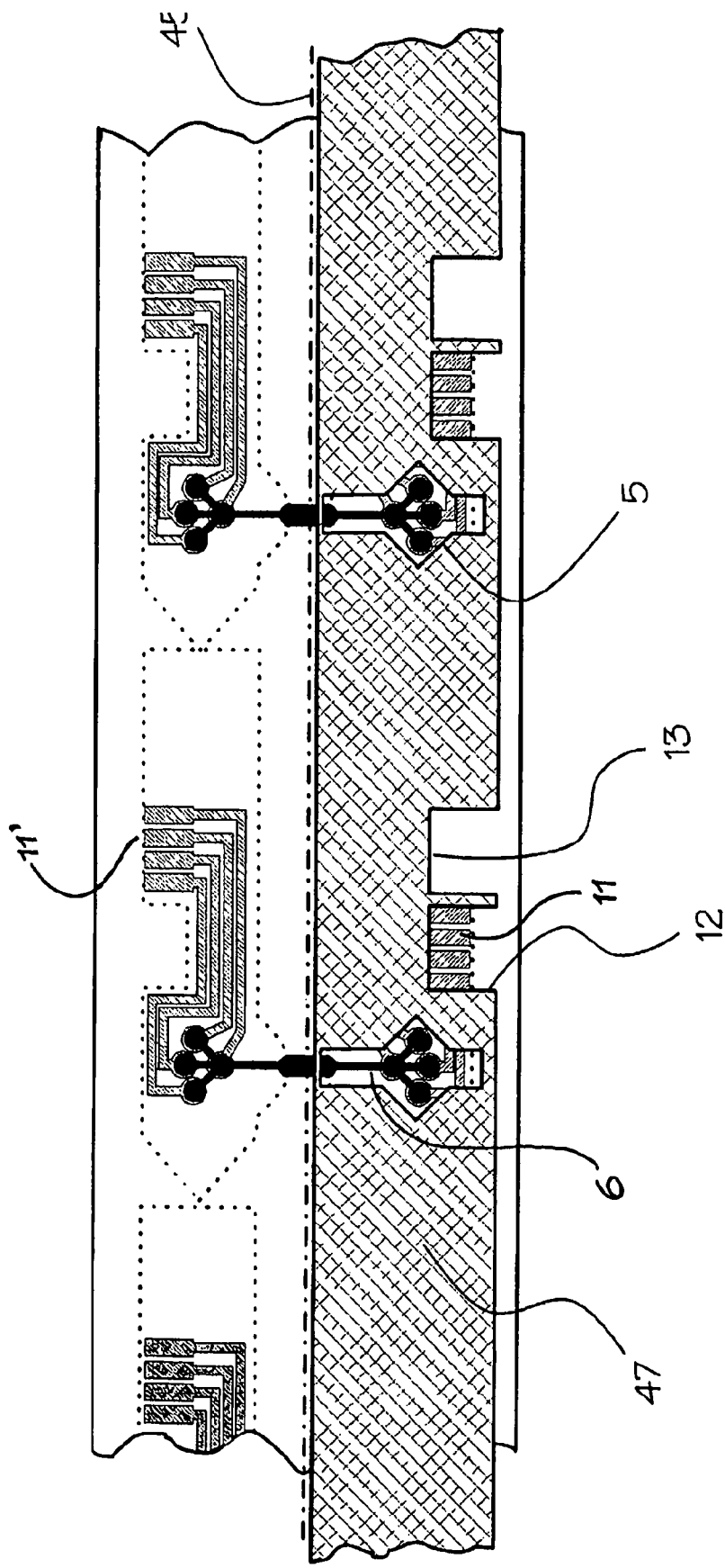

The task to register the centre layer providing the space between base and cover layer becomes less critical due to the large discontinuity 5 furnished in the centre layer, which gives enough tolerance in the production process for a continuous manufacturing schema as shown in FIG. 5*b*. In case the centre layer 47 is printed it could be applied as last step during the flexographic printing of the analyte test element. Various Bonding methods are available to join base and cover layer manufactured with a printed centre layer 47. Most suitable are heat sealing, laser bonding or ultrasound welding. Alternatively, an additionally layer 47 which may be formed of double-sided adhesive tape is laminated on one of the surfaces, e. g. the surface 2*a* of the base layer 2.

The centre layer 47 which defines the distance between the first and second surface of the base and cover layers, provides breakthroughs 5, 12, 13 exposing the sample distribution system 6 and the contacts of the electrodes 11, 11' and creates a cavity for the sample distribution systems in the analyte test element after the final assembly step.

Figure 5C:
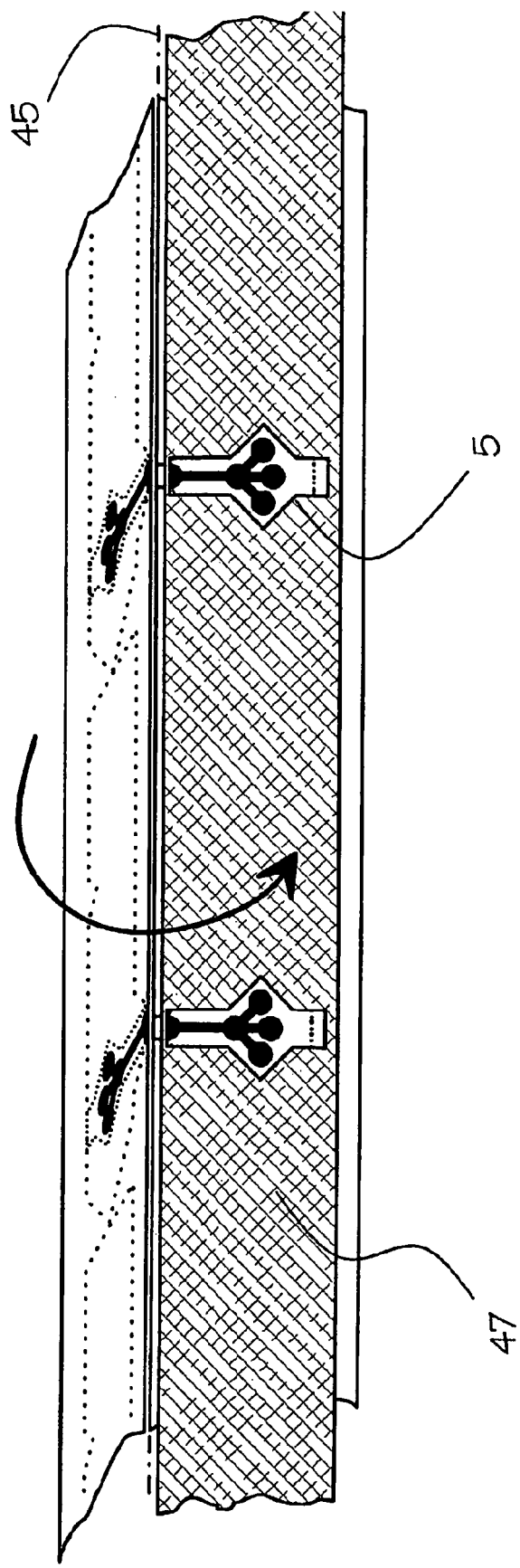
Figure 5D:
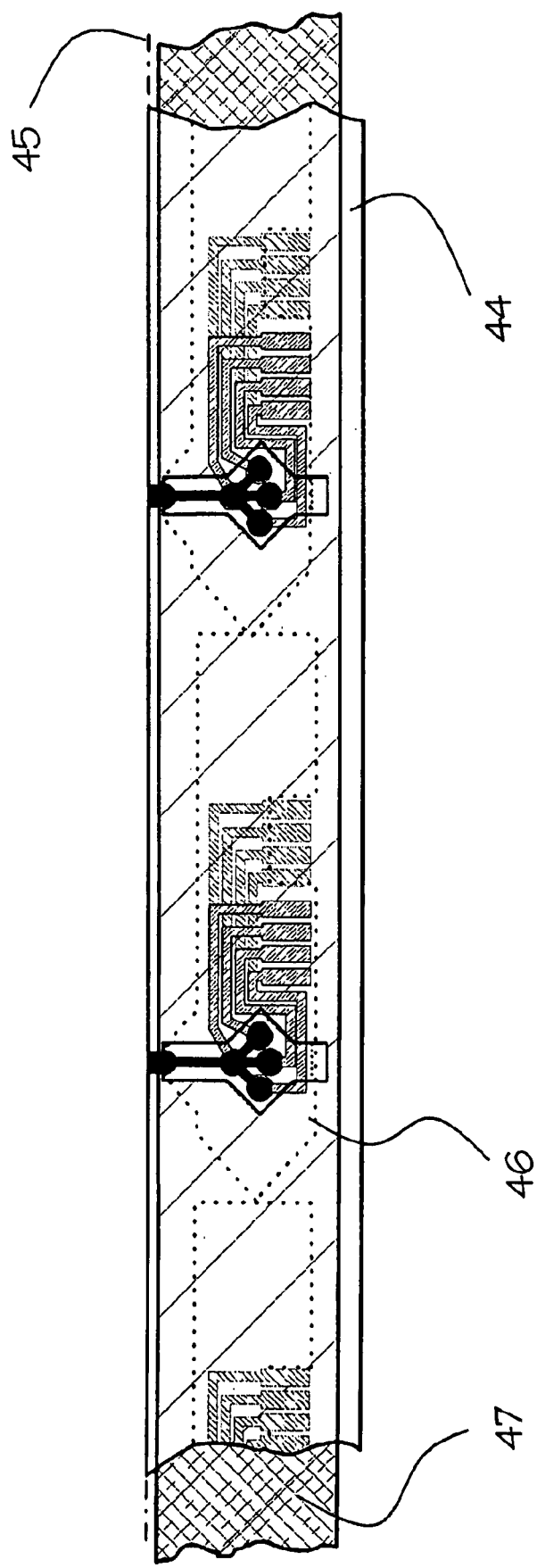

Final assembly of the analyte test element is shown in FIGS. 5*c* and 5*d*. The analyte test element is assembled by folding the upper half of the web substrate 44 along the fold line 45 on the lower part of the web substrate, e. g. with help of a folding iron, as illustrated in FIG. 5*c* creating a sandwich type web as shown in FIG. 5*d*. Subsequently, a press roller can secure a tight connection between the centre layer, base and cover layers.

Finally, the laminated web is cutted or punched into the desired product shape, whereas line 46 projects an exemplary shape of the final analyte test strip onto the web before the segregation process. With the preparation method illustrated in FIG. 5 the top part of the substrate can be folded on to the bottom part without the danger of loosing the registration in the x-direction of the web and provides an easier method to get the right registration of the first and second surfaces forming the sample distribution system in comparison to single sheet process.

The volume requirement for the sample distribution system contained in the analyte test element of the preferred embodiment is approximately 0.5 µL-1.0 µL and requires roughly 100 nL-150 nL per detection area. Nevertheless, it will be obvious for the one skilled in the art that the volume of the sample distribution system will vary with various designs and with the number of employed predetermined detection areas as well as with the thickness of the centre layer 3.

FIG. 6 shows various patterns of the different sample distribution systems. Cell AI in FIG. 6 illustrates the cases for a simple sample distribution system suitable to perform a linear calibration. Column A of FIG. 6 shows the principal design of sample distribution systems with no background correction, whereas column B provides designs for sample distribution systems with background corrections. Column C indicates the highest order of the polynomial calibration equation achievable with the adjacent designs, and column n indicates the minimum number of predetermined detection areas on each surface, respectively the number of required measurements. The literals in each design indicate the position of the background correction (c), sample (1), and all associated calibration areas (2, 3, 4, 5, 6) with increasing amounts of calibration compound. The simplest calibration is represented by a linear equation where the relationship between measurement and the analyte concentration is strictly proportional. The calibration of the analyte test element is generally performed using the standard addition method by adding a known amount of calibration compound to the sample fluid provided on the different calibration areas and subsequent calculation of a linear or monotone non-linear calibration equation.

Figure 7:
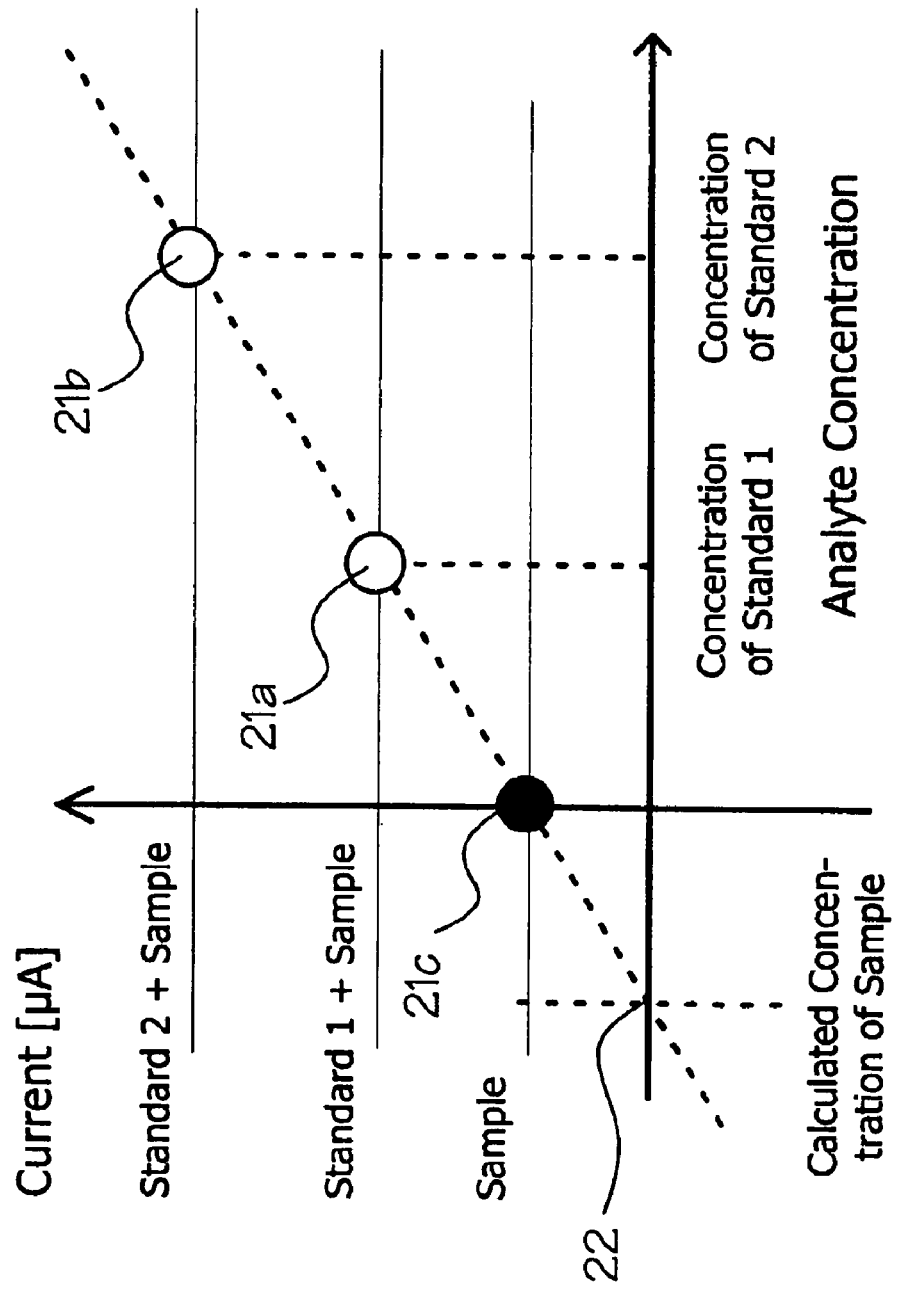
FIG. 7 is a graph showing the calculation of the sample analyte concentration using the standard addition method.

FIG. 7 gives a more detailed explanation about case I. The calibration model or order (column C) needs to be appropriate for the selected analyte and employed detection chemistry, consequently it is not possible to apply a linear calibration model to a chemical reaction which obeys a fourth order model and vice versa. However, it is still possible to use the analyte test element designed for five standard additions for a linear calibration, the higher amount of standards will allow an even more precise measurement and a statistical validation with higher significance in terms of correlation coefficient, standard deviation and standard error of the test compared to a linear calibration based on two standards.

Moreover, the repetition of sample and standard measurements is possible as well, thus it is possible to perform two independent linear calibrations for one particular sample of physiological fluid with the embodiments shown in row IV. Likewise, it is possible to use the same analyte test element for the determination of two analytes.

Alternatively, a multi analyte system can be realised within the same set of predetermined detection areas if the selected detection chemistries generates no interference problems and the reaction educts and products of one reaction will not take part in the other reaction. Furthermore, it is necessary that the redox-active reaction products can be determined independently at two different electrode potentials. Within this detection schema, the product reacting at a low potential will be determined first before the measurement device is switched to the higher potential to monitor the second product. Thus, the analysis has to be carried out in a sequential manner, which will require more time compared to the case described above.

If the analyte test element is designed to perform n determinations, whereby n is an integer number larger than 2, all of the n detection areas 6*a* on the first surface 2*a* are coated with the catalytic formulation (enzyme-mediator-layer 18) promoting the detection of the analyte in the physiologic sample fluid, whereas n predetermined detection areas 6'*a* on the second surface 4*a* of calibration compound or analyte and m blank formulations, whereby m is an integer number of at least 1, and n>m. In other words, at least one of the n detection areas of the sample distribution system does not contain the calibration compound.

After the physiological fluid is applied to the sample application area and distributed to the predetermined detection areas by capillary action, it dissolves the catalytic formulations on the n predetermined detection areas 6*a* of the first surface 2*a* as well as the n calibration formulations on the n predetermined detection areas 6'*a* of the second surface 4*a* forming a mixture of analyte, calibration compound (which could be identical with the analyte), enzyme and mediator. Within these n mixtures the concentration of the electrochemically detectable species is changing proportional to the different levels of calibration compound plus the unknown level of analyte, thus allowing the determination of n results by an electrochemical detection means and the calculation of the analyte concentration. Preferably, the catalytic formulation and the calibration formulations applied to the predetermined detection areas are readily soluble by a physiological fluid or other aqueous solutions. Both formulations provided on the detection areas opposing each other are positioned in close proximity to facilitate rapid diffusive mixing of the components to allow a fast reaction of all chemical compounds contained in the detection areas and to expedite a fast electrochemical determination of the analyte concentration.

Since there are more than two detection areas arranged within the sample distribution system, whereby at least two of the detection areas contain known but different levels of calibration compound, it is possible for the processing means to calculate the unknown concentration of the analyte from the n measurements performed with the physiological fluid in the analyte test element.

FIG. 7 shows an exemplary calculation of an analyte concentration in a sample by the linear standard addition method, a known calibration technique used in various fields of analytical chemistry, and now integrated and used in a dry reagent test strip for electrochemical detection for the first time. In this example, the sample distribution system includes three analyte detection areas, two are coated with different predetermined levels of a calibration compound. After applying the physiological fluid to the sample distribution system, the catalytic reaction takes place in the analyte detection areas, and the electrochemical detection means measures a first electrochemical signal $21a$, such as the electrical current generated by the sample located in the detection area with the first level of calibration compound. The readout of this detection area represents a signal proportional to the combined concentration of the first calibration compound and the concentration of the analyte. In parallel, a second electrochemical signal $21b$ is produced by the sample located in the detection area with the second level of calibration compound representing a signal proportional to the combined concentration of the second calibration compound and the concentration of the analyte. Furthermore, a third electrochemical signal $21c$ is measured in the detection area containing only the sample with unknown analyte concentration.

Since there is a linear correlation between the electrochemical signal and the concentration of the analyte, the processing means of the analyte test system can calculate by linear regression analysis of the measurements the coefficients for the calibration equation $y=c_0+c_1 x$ in the example above. The concentration of the analyte in physiological fluid sample is determined by the zero point ($y=0$) $22$ of the previously calculated calibration equation.

A general representation of applicable calibration equations is given in form of:

$$y = \sum_{1}^{n-1} \{c_{(n-1)} x^{(n-1)}\}$$

with $y=f$ (results of the electrochemical measurement); $x=f$ (concentration of the calibration compounds); n number of measurements excluding repetitions or background measurements.

This polynomial equation format provides in conjunction with the n-values presented in FIG. 6 the entity of most useful calibration models for the various designs of the sample distribution systems in the aforementioned figure. The values for y and x may represent data calculated by a function to allow pre-processing of raw data generated by the detection mean. Thus, it is possible to use a logarithmic function for linearisation of raw data.

It should be obvious from the discussion that the invention is not limited to the designs of sample distribution systems in FIG. 6; and someone skilled in the art becomes able to design a systems with n larger than 6 in conjunction with the provided information.

A detailed introduction in linear and non-linear standard addition methodology is given by Frank et al. (Anal. Chem., Vol. 50, No. 9, August 1978) and Saxberg et al. (Anal. Chem. Vol. 51, No 7, June 1979).

A preferred embodiment of the analyte test element of the present invention according to FIG. 3 is designed to comprise one detection area, which includes the catalytic compounds but no calibration compound ($6a_1$ and $6'a_1$, resp.), one detection area which includes the catalytic compounds and a first concentration of the calibration compound ($6a_2$ and $6'a_2$, resp.), one detection area which includes the catalytic compounds and a second concentration of the calibration compound ($6a_3$ and $6'a_3$, resp.) and one detection area for the background absorption ($6c$ and $6'c$, resp.). By means of the latter detection area, which includes neither a calibration compound nor catalytic compounds, it is possible to determine the background absorption of the sample and to consider it during the calibration process.

Figure 8:
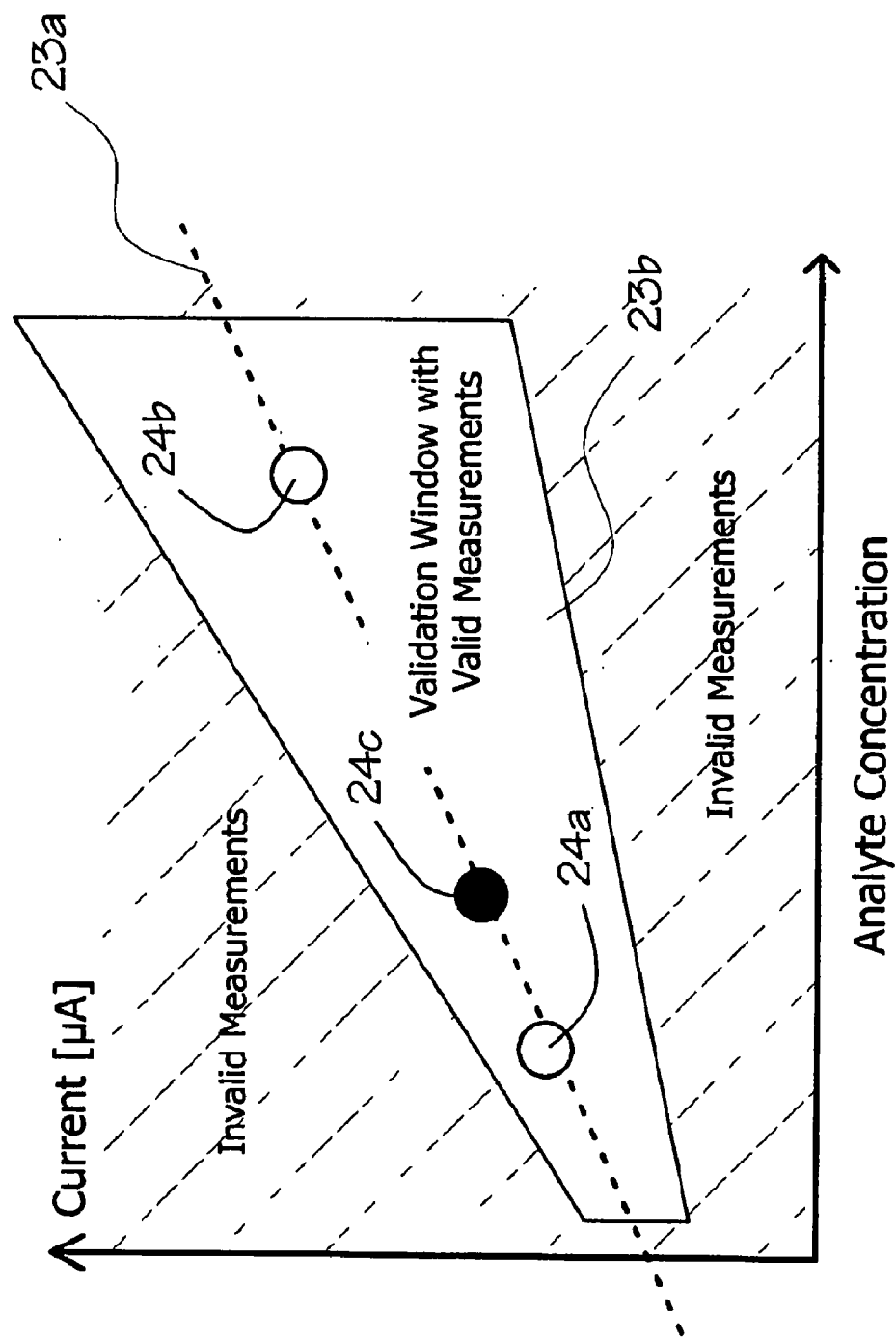
FIG. 8 is a graph showing the validation method for the calculated results and calibration data.

FIG. 8 illustrates a pre-programmed validation method for calculated results and calibration data, whereby the validity of the measured results is verified by defining a "validation window" $23b$ for valid and correct measurements. By this means, the analyte test system can constrain all data to a validated and useful concentration range, e. g. 30 to 600 mg/dL glucose, and a valid range for the electrochemical signal typically between 0 and 5 µA depending on the electrode material, mediator, potential and electrode area. Likewise, the processing means can constrain the slope and the intercept or more general the coefficients $c_0$ to $c_{(n-1)}$ to a valid range, which is particularly useful for non-linear polynomial equations. A population of valid measurements with a corresponding calibration line $23a$ located within the boundaries of the validation window $23b$ is illustrated in FIG. 8; see literals $24a$ to $24c$.

Even more powerful is the validation of results by means of statistical evaluation and linear regression analysis. The quality of the calibration can be judged by a correlation coefficient $r^2$ and a confidence interval, thus the analyte test system can refuse to display a measurement result if the correlation coefficient falls below a pre-programmed threshold. Alternatively, the processing means can calculate a tolerance or concentration range of the result based on the calculated confidence interval. These methods allow a high control over the quality of results provided to the patient, which is used and known today only from sophisticate and expensive laboratory methods and equipment. Even more important for the patient/user is, especially in hospital settings, the quality assurance right at the time of the measurement.

Figure 9:
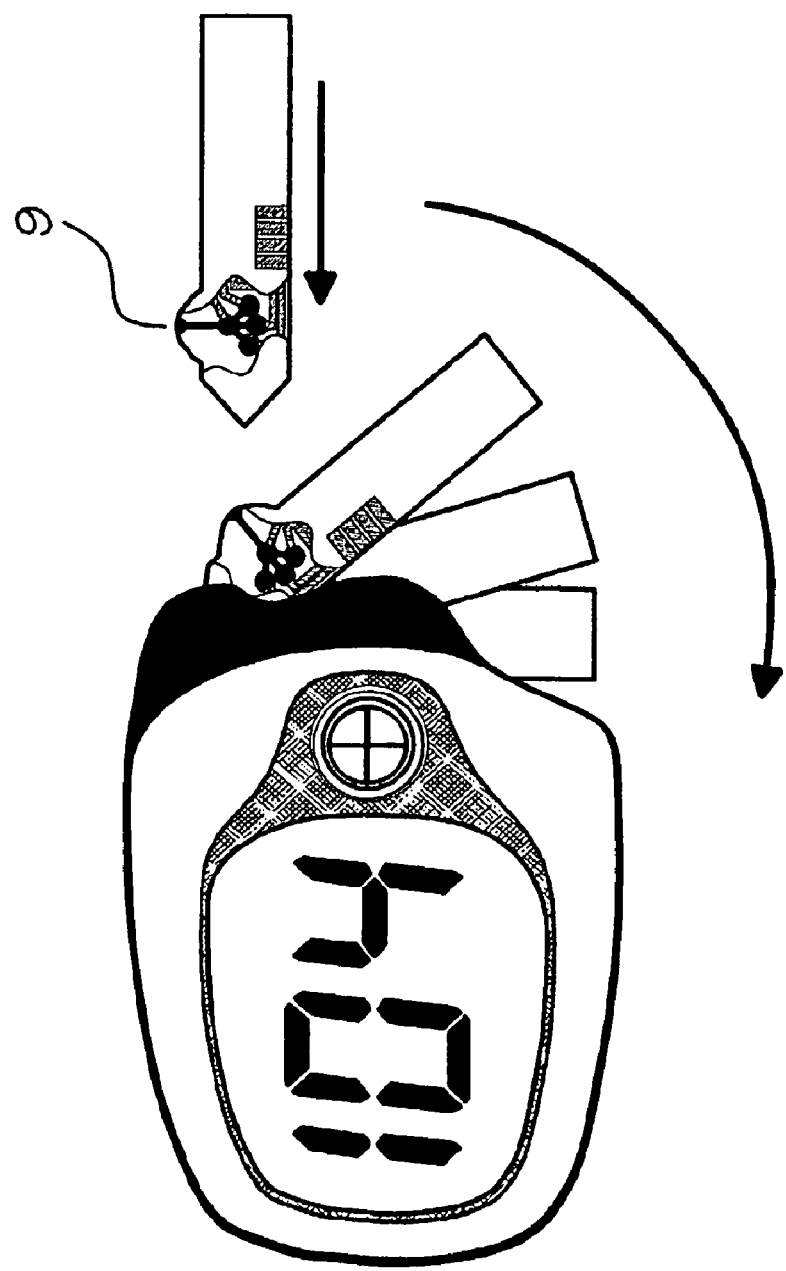
FIG. 9 shows an exemplary application of an inventive test strip with a meter.
Figure 10:
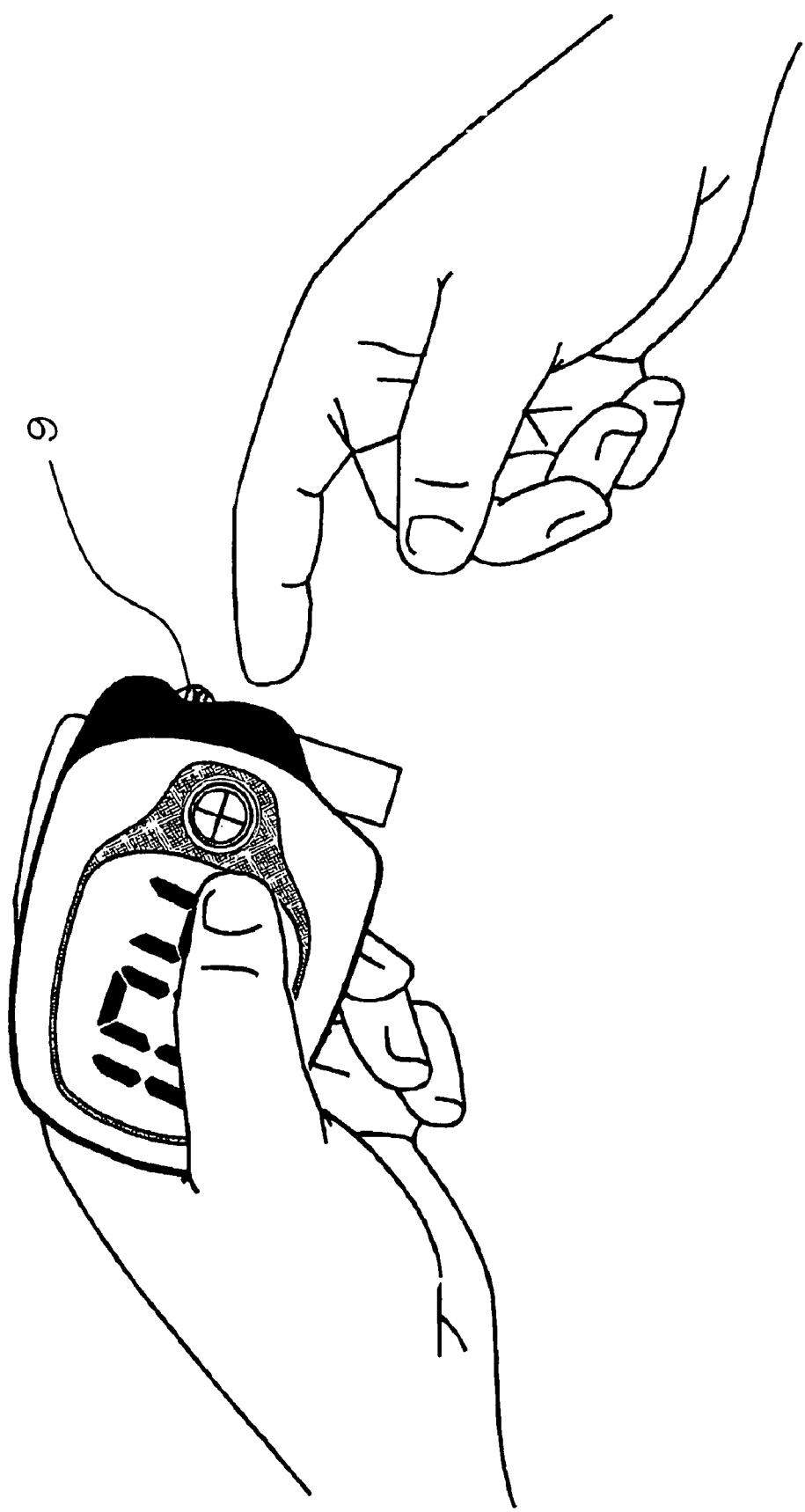
FIG. 10 shows the analyte test system with an inserted analyte test strip ready to receive a sample of capillary blood from the finger tip of a patient.

FIG. 9 shows the insertion of the analyte test strip into an analyte test system. In a preferred embodiment the analyte test strip is designed to have a lateral and concave extension located on one major side of the test strip where the sample application area 9 resides. This feature allows easy application of capillary blood samples from the patients arm or finger as shown in FIG. 10.

Figure 11:
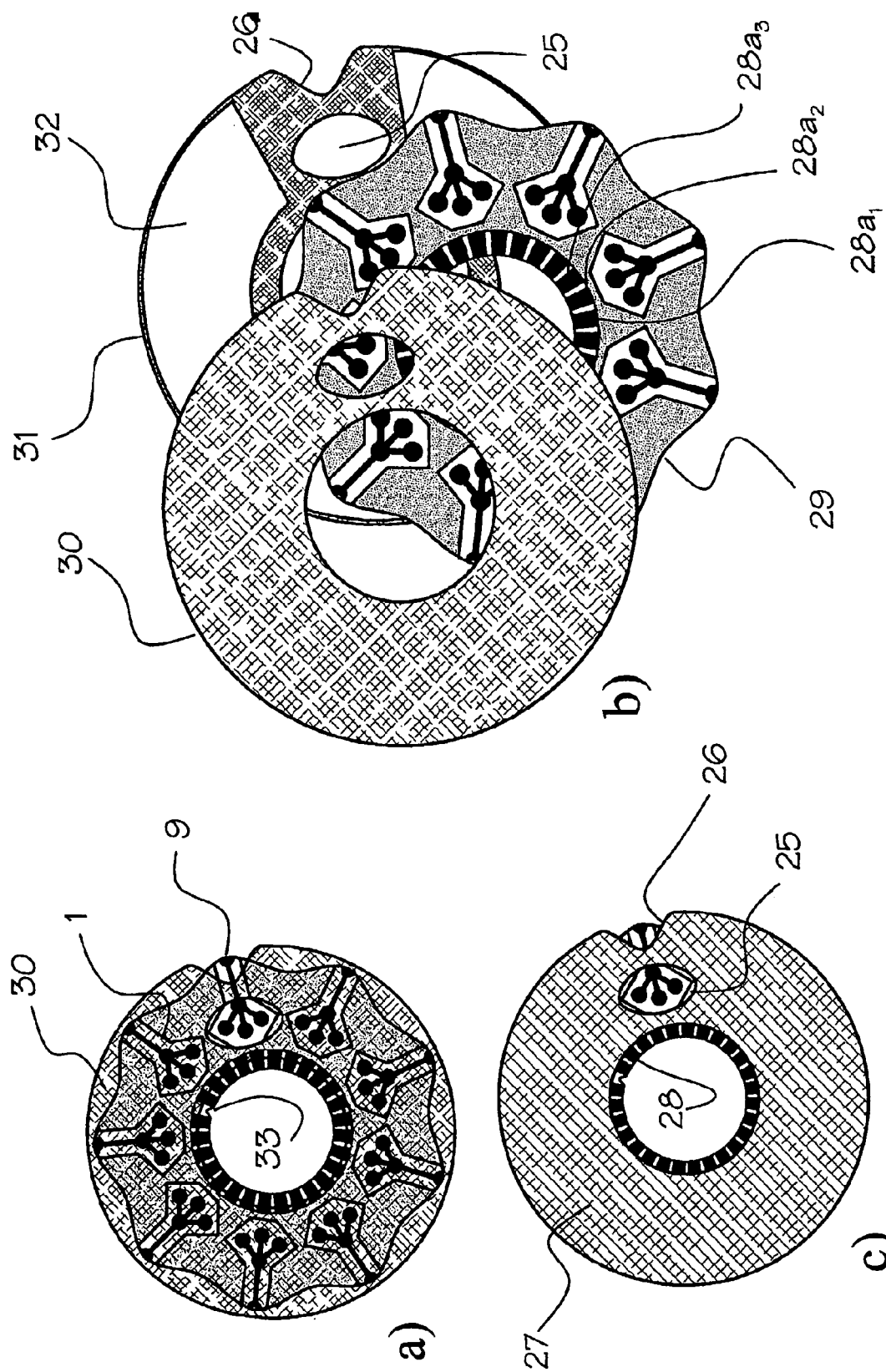
FIG. 11 shows the construction of an analyte test disk.

In another embodiment of the present invention, as shown in FIG. 11, a plurality of analyte test elements is arranged symmetrically around a centre point to form an analyte test disk 29 with outward facing sample application areas 9. The exemplary analyte test disk 29 according to FIG. 11a includes nine analyte test elements 1 of the present invention. As shown in the exploded view of FIG. 11b, the analyte test disk 29 is covered by a disk cover or sleeve composed of a top layer 30 and a bottom layer 31. The inner side of the top and bottom layer 30, 31 of the sleeve may also be provided with a moisture-absorbing layer 32 to capture the excess of blood after the analyte test element has been used and transported inside the cartridge system. The top layer 30 and bottom layer 31 of the disk cover have breakthroughs which are arranged congruently to each other, forming an optical window 25 to expose the active analyte test element and to assist the user to insert the disk into the meter in the right orientation. Adjacent to the optical window 25 in the outer peripheral areas of the disk cover top layer 30 and the disk cover bottom layer 31 are two recesses 26 to expose the sample application area 9 of the analyte test elements of the disk. The contacts 28a to the working electrode system of the analyte test element and the contacts 28'a (not shown) to the reference electrode system, which are provided on the opposite site from the contacts 28a, are aligned to the interior edge of the disk 29 to expose them to the meter. Preferably, the test disk 29 is additionally provided with a registration notch 33 which may also be located in the interior edge of the disk 29. During a measurement procedure, only the analyte test element, which is currently used for the analyte determination is exposed by the recess 26, as shown in FIG. 11c. The analyte test disk 29 is able to rotate around its centre point to bring a new analyte test element into position as required.

Figure 12:
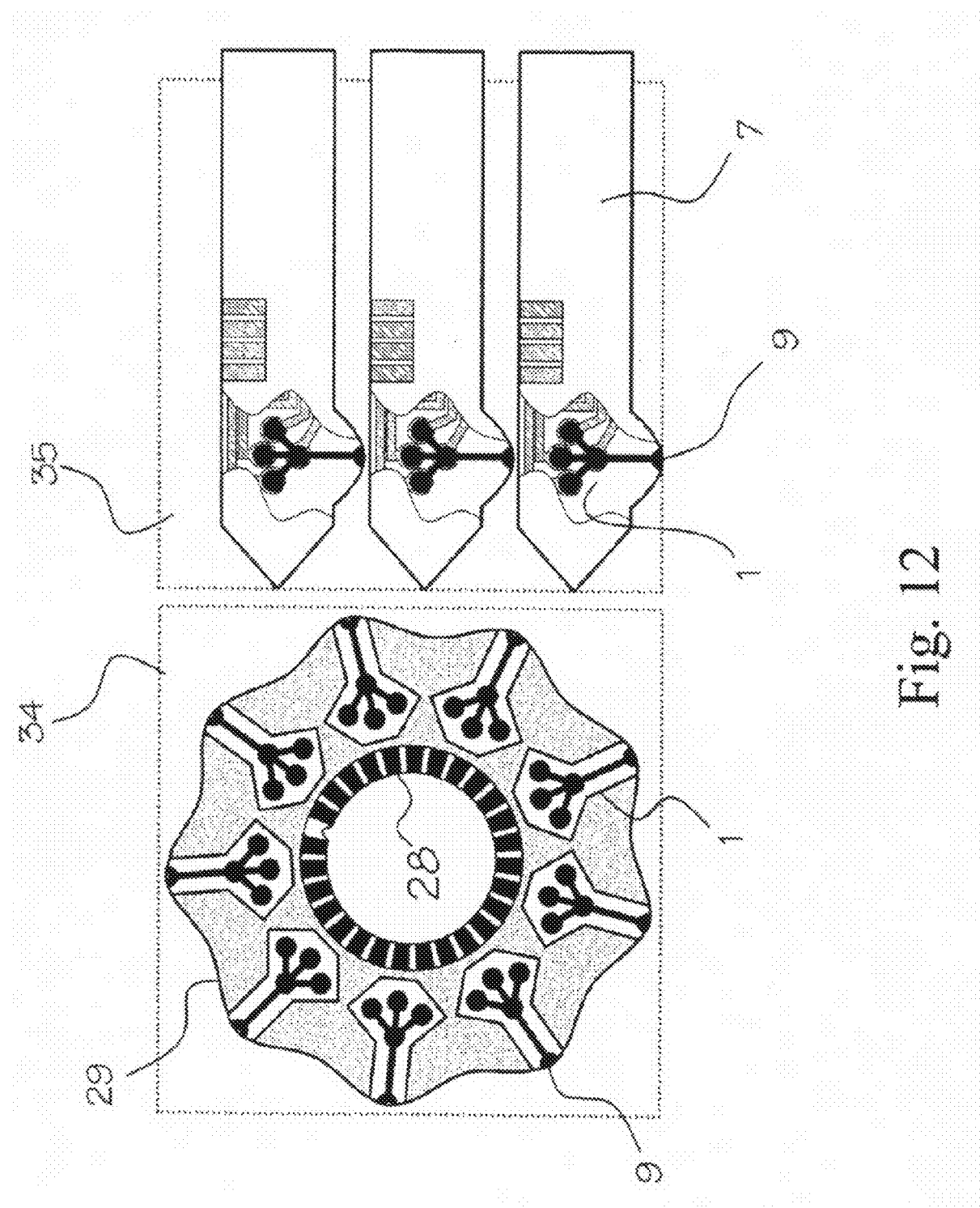
FIG. 12 shows an analyte test disk compared to an analyte test strip.

By means of an analyte test disk, it is possible to arrange a plurality of analyte test elements in a relatively small area. The same number of analyte test elements included in analyte test strips would require a much larger area and thus much more material, as illustrated by the size comparison of analyte test disk and analyte test strips illustrated in FIG. 12. Whereas the unit area 34 of the analyte test disk 29 includes nine analyte test elements 1, the identical area 35 would accommodate only three analyte test elements incorporated in three analyte test strips 1. However, a reduction of the test strip sizes is not advisable due to the problematical handling of smaller strips which becomes difficult and more impractical for the patient.

Figure 13:
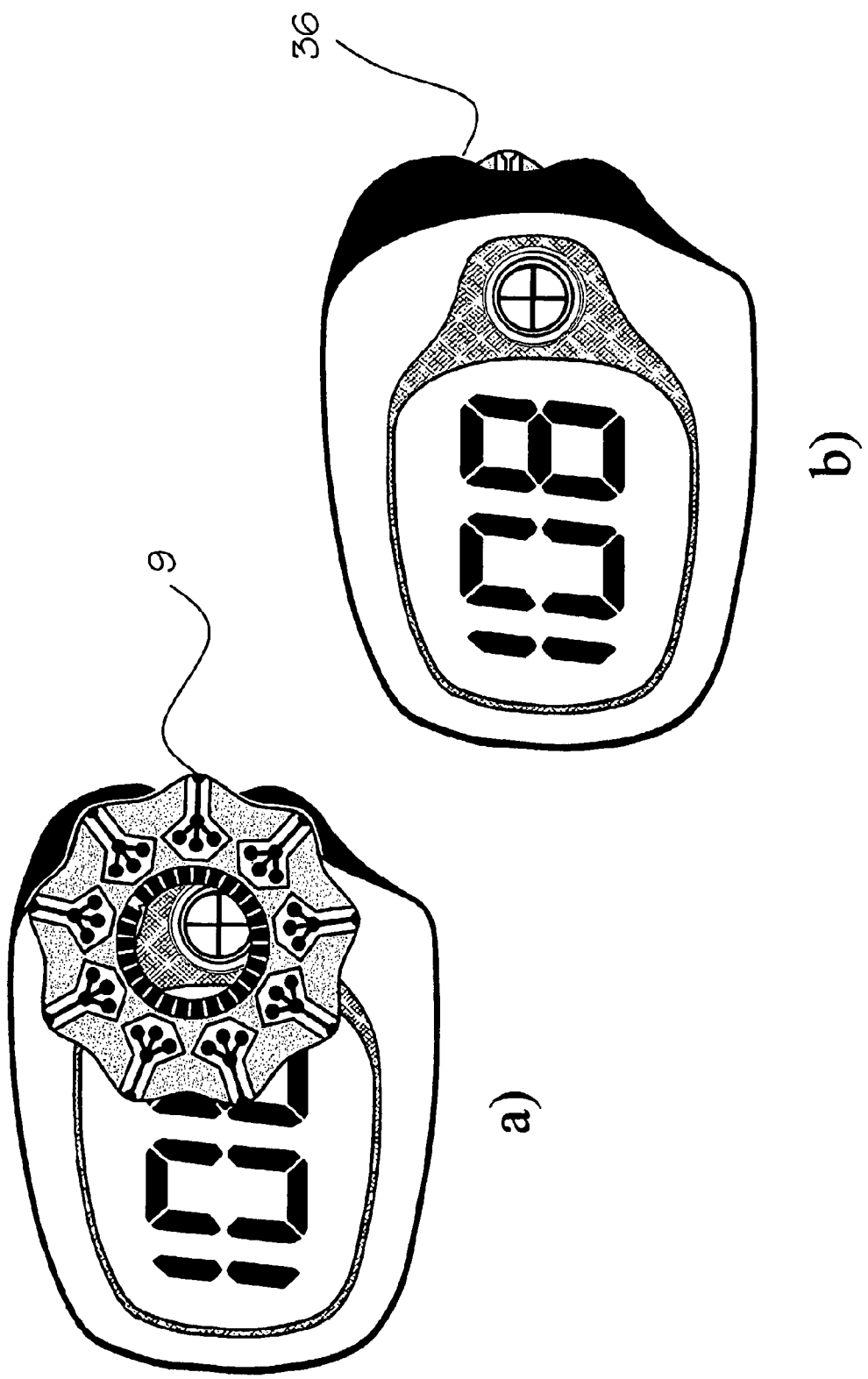
FIG. 13 shows a analyte test system with an integrated analyte test disk.

FIG. 13a and FIG. 13b show the analyte test disk included in a meter, whereby the sample application area 9 again protrudes from the meter housing 36.

Figure 14:
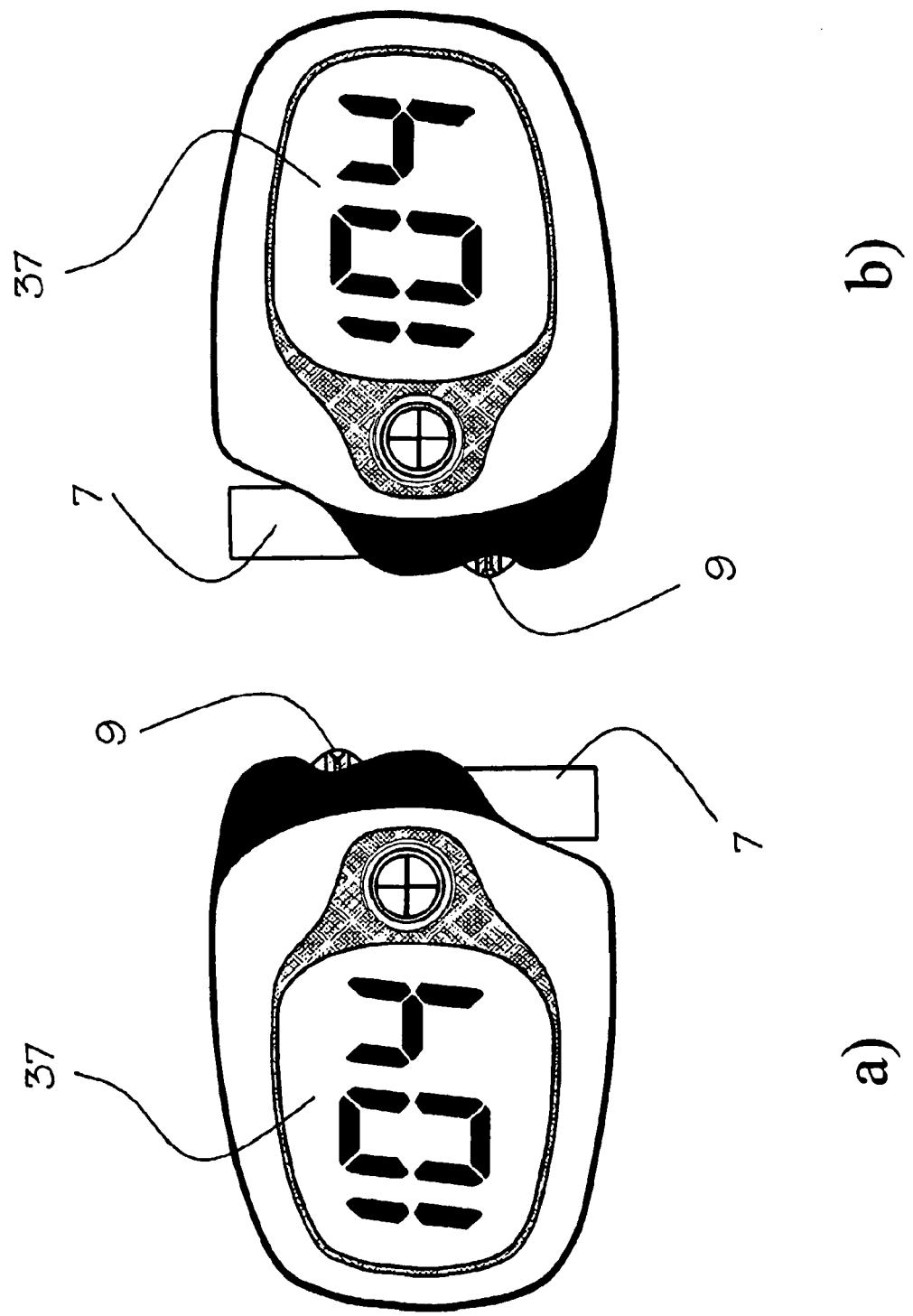
FIG. 14 shows a analyte test system with an analyte test strip in left hand and right hand handling mode.

Not only for the analyte test strips but also for the analyte test disk it is possible to adapt the measurement device (analyte test system) to a left hand and right hand handling mode as illustrated in FIG. 14. When a left hand handling mode is desired according to FIG. 14a, the analyte test strip 7 is inserted into the meter from the bottom side, the sample application area 9 for receiving the physiological fluid protruding from the meter housing. After completion of the measurement, the analyte concentration is presented on the analyte test system display 37. Likewise, a right hand handling mode according to FIG. 14b can be realized by adapting the display 37 of the analyte test system to a converse mode of operation by rotating the displayed content on the display by 180°, enabling the insertion of the analyte test strip 7 into the meter from the top side.

Figure 15:
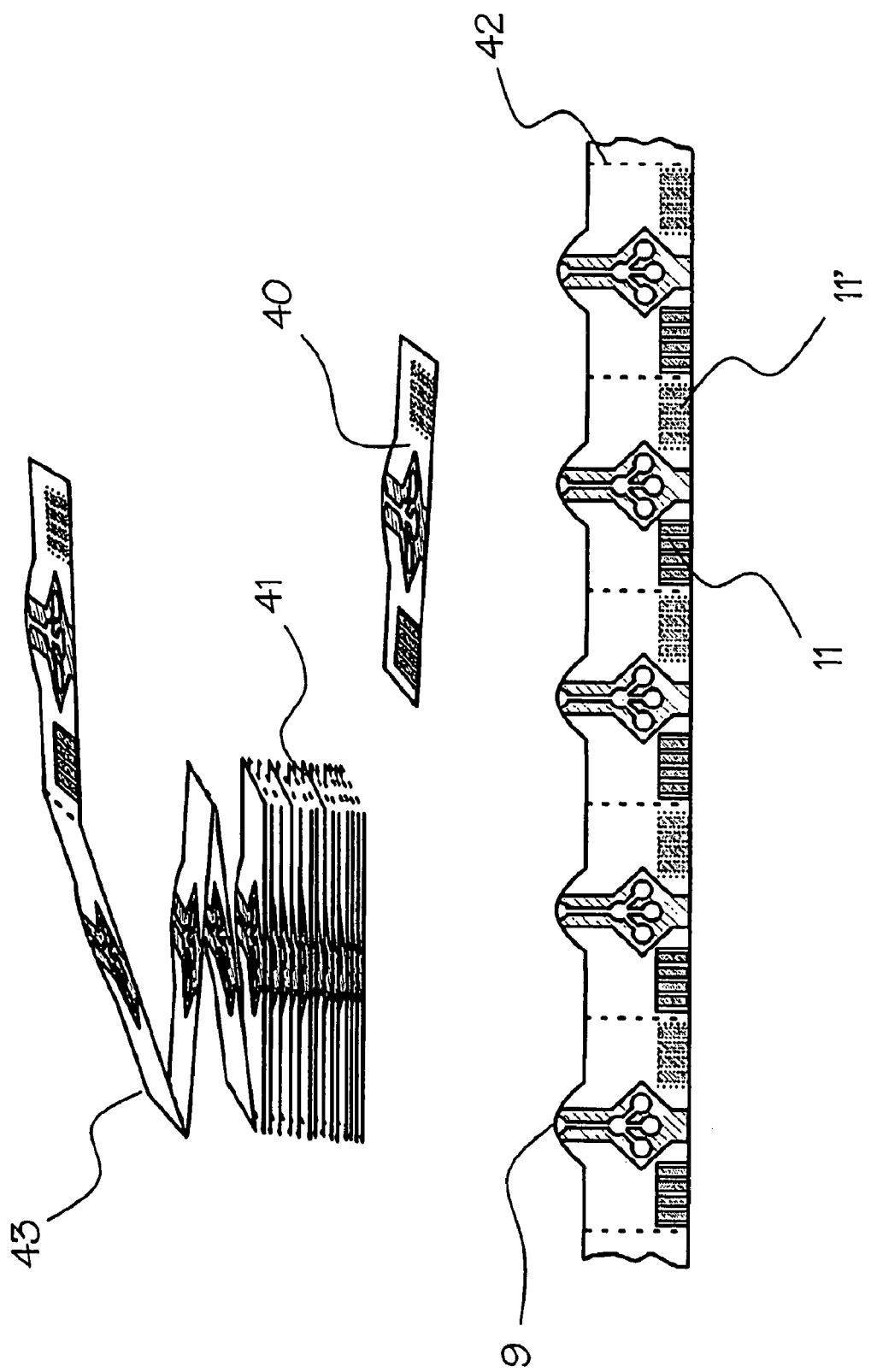
FIG. 15 shows an analyte test bandolier and folded bandolier to build a stack.

FIG. 15 illustrates another possibility to arrange the analyte test elements in a space-saving manner. In this embodiment the analyte test elements are arranged side by side to form a analyte test bandolier 43 with a lateral extension to form the sample application areas 9. In the bandolier, the area between two analyte test elements is provided with a perforation or break line 42 to separate a single analyte test element 40 from the analyte test bandolier 43. By means of a zigzag-folding along the perforation or break lines 42 it is possible to build an analyte test device bandolier stack 41 which can easily housed in a small container to allow an easier dispensing of the single analyte test elements of the analyte test bandolier 43.

The analyte test element of the present invention, produced in disk or strip form, can easily be prepared by processes to those of ordinary skill in the arts of printing, die punching, and laminating. The design of the analyte test element allows a simple and cost efficient production process, which is preferably but not necessarily of a continuous nature.

Due to the integrated calibration procedure and validation method, the analyte test system of the present invention provides reliable results by compensating endogenous interferences, such as different blood types and haematocrit levels, as well as exogenous interferences, such as nutrition supplements like Vitamin C or pharmaceuticals, which otherwise would influence and modify the measuring results. Since the calibration of the analyte test system is done in parallel to the measurements, different environmental parameters, such as temperature at the time of actual measurement, are of no consequence for the accuracy of the determined results. Further, production variations, e. g. variations in the thickness of the centre layer, are compensated by the integrated calibration procedure as well as degradation of chemical or biochemical compounds such as enzymes or mediators. The loss of enzyme activity is detectable due to the internal calibration and can be compensated to a certain extend which leads to a prolonged shelf live of the product. This is especially an advantage in diagnostic systems, which require more sensitive biocatalysts than glucose oxidase.

The present invention provides an analyte test system that incorporates calibration and quality control means with electrochemical detection means in a dry reagent test element that does not make excessive demand on the production process but eliminates the need for user interventions in calibration and quality control procedures in combination with a tight control of the strip performance at time of sample analysis.

The invention claimed is:

1. An analyte test element for determining the concentration of at least one analyte in a physiological or aqueous sample fluid having a first surface (2a) and a second surface (4a) opposite from each other, said first and second surfaces are provided with two equivalent patterns, forming areas of high and low surface energy, which are aligned mostly congruent, whereby the areas of high surface energy (6, 6') create a sample distribution system with at least two detection areas (6a, 6'a), characterized in that the detection areas (6a) of the first surface (2a) are provided with working electrodes (8a) and the detection areas (6'a) of the second surface (4a) are provided with corresponding reference electrodes (8'a) of electrochemical detection means, wherein n predetermined detection areas (6a) covering the working electrodes (8a) of said first surface (2a) are coated with a catalytic formulation promoting the electrochemical detection of an analyte in a physiological fluid, and n predetermined detection areas (6'a) covering the reference electrodes (8'a) of said second surface (4a) are coated with n calibration formulations made up of m blank formulations and n−m formulations with different levels of calibration compound, whereby n is an integer number larger than 2, m is an integer number equal or larger than 1, and n>m.

2. The analyte test element according to claim 1, wherein the distance between the first and second surface is determined by a center layer (3), which is arranged between a base layer (2) and a cover layer (4) having the first and second surfaces (2a, 4a).

3. The analyte test element according to claim 2, wherein the center layer (3) has a discontinuity (5) to form a hollow cavity together with the first and second surface (2a, 4a) of the base and cover layer (2, 4), said hollow cavity being larger than the sample distribution system formed by the areas of high surface energy (6, 6') on the first and second surfaces (2a, 4a).

4. The analyte test element according to claim 1, wherein said areas of high surface energy (6, 6') are created by a water insoluble hydrophilic composition applied on the first and second surfaces (2a, 4a).

5. The analyte test element according to claim 1, wherein said areas of high surface energy (6, 6') on first and second surfaces (2a, 4a) are restricted by hydrophobic insulating layers (14, 14') providing areas with low surface energy.

6. The analyte test element according to claim 1, wherein an additional detection area (6c) is provided, which neither contains the catalytic compound nor the calibration compound, enabling the measurement of background signals.

7. The analyte test element according to claim 1, wherein said calibration compound contained in the calibration formulation coated on n–m predetermined detection areas (6'a) of second surface (4a) is identical or substantially equivalent to the analyte and able to induce the same chemical reaction in the catalytic formulation as the analyte in the physiological fluid sample.

8. The analyte test element according to claim 7, wherein the calibration compound is glucose.

9. The analyte test element according to claim 1, wherein the catalytic formulation contains as reactive components a promoter undergoing a catalytic or non-catalytic reaction with the analyte, and/or a co-enzyme, and a mediator generating an electrochemical signal at the surface of an electrode.

10. The analyte test element according to claim 9, wherein the promoter is an enzyme selected from the group consisting of dehydrogenases, kinases, oxidases, phosphatases, reductases and/or transferases.

11. The analyte test element according to claim 10, wherein the promoter is an enzyme specific for glucose.

12. The analyte test element according to claim 9, wherein the mediator to determine the analyte concentration is selected from the group consisting of potassium hexacyanoferrate (III), tetracyano-p-quinone-di-methane (TCNQ), methylviologen ($MV2^+$ tetrathiafulavlene (TTF), N-methylphenzinium ($NMP^+$), ruthenium (III) hexamine, osmium bipyridine, ferrocene or their derivates.

13. The analyte test element according to claim 1, which is provided in form of a strip, wherein a sample application area (9) is located at the end of a convex and lateral extension (10) on one side of said analyte test strip.

14. An analyte test arrangement including a plurality of analyte test elements according to claim 1, which are arranged symmetrically around a center point to form an analyte test disk (29) with outward facing sample application areas (9).

15. An analyte test arrangement including a plurality of elements according to claim 1, which are arranged in a linear manner to form an analyte test bandolier (43) with lateral extensions forming the sample application areas (9).

* * * * *